United States Patent
Caldarella et al.

(10) Patent No.: US 10,080,599 B2
(45) Date of Patent: Sep. 25, 2018

(54) BONE FUSION/FIXATION DEVICE AND RELATED SYSTEMS AND METHODS

(71) Applicant: Surgical Design Innovations, Grimes, IA (US)

(72) Inventors: David Caldarella, Barrington, RI (US); Michael Lee, Grimes, IA (US); Shannon Rush, Pleasanton, CA (US); Jordan Grossman, Cuyahoga Falls, OH (US); John Roop, Oak Park, IL (US); Christopher Pell, San Francisco, CA (US)

(73) Assignee: SurgicalDesignInnovations, Grimes, IA (US)

( * ) Notice: Subject to any disclaimer, the term of this patent is extended or adjusted under 35 U.S.C. 154(b) by 98 days.

(21) Appl. No.: 15/121,239

(22) PCT Filed: Feb. 27, 2015

(86) PCT No.: PCT/US2015/018111
§ 371 (c)(1),
(2) Date: Aug. 24, 2016

(87) PCT Pub. No.: WO2015/131106
PCT Pub. Date: Sep. 3, 2015

(65) Prior Publication Data
US 2016/0367300 A1 Dec. 22, 2016

Related U.S. Application Data

(60) Provisional application No. 61/945,511, filed on Feb. 27, 2014.

(51) Int. Cl.
*A61B 17/80* (2006.01)
*A61B 17/72* (2006.01)
(Continued)

(52) U.S. Cl.
CPC ...... *A61B 17/8061* (2013.01); *A61B 17/7291* (2013.01); *A61B 17/808* (2013.01);
(Continued)

(58) Field of Classification Search
CPC .............. A61B 17/8061; A61B 17/809; A61B 17/7291; A61B 17/808; A61B 17/8009; A61B 17/8863; A61B 17/82
See application file for complete search history.

(56) References Cited

U.S. PATENT DOCUMENTS 5,201,737 A * 4/1993 Leibinger ............ A61B 17/688
606/280
5,250,048 A * 10/1993 Gundolf ............. A61B 17/8085
606/297
(Continued)

FOREIGN PATENT DOCUMENTS

| CN | 201617934 U | 11/2010 |
|---|---|---|
| GB | 2331244 A | 5/1999 |

*Primary Examiner* — Christian Sevilla
(74) *Attorney, Agent, or Firm* — Davis, Brown, Koehm, Shors & Roberts, P.C.; Sean D. Solberg

(57) ABSTRACT

The various embodiments disclosed herein relate to bone fixation or fusion devices, including intramedullary fixation or fusion devices that are implanted around the target bone. Certain device embodiments relates to devices that can be bent or otherwise deformed to replicate the natural or desired curve of the bone or joint being treated. In addition, other embodiments relate to implantation devices that can be used to implant or position the bone fixation or fusion devices.

26 Claims, 34 Drawing Sheets

(51) Int. Cl.
*A61B 17/82* (2006.01)
*A61B 17/88* (2006.01)

(52) U.S. Cl.
CPC ........ *A61B 17/809* (2013.01); *A61B 17/8085* (2013.01); *A61B 17/82* (2013.01); *A61B 17/8863* (2013.01); *A61B 17/8009* (2013.01)

(56) References Cited

U.S. PATENT DOCUMENTS

| | | | |
|---|---|---|---|
| 5,718,705 A * | 2/1998 | Sammarco | A61B 17/8085 606/260 |
| 6,123,709 A * | 9/2000 | Jones | A61B 17/1728 606/280 |
| 6,336,928 B1 | 1/2002 | Guerin et al. | |
| 2003/0100898 A1 | 5/2003 | Wellisz | |
| 2007/0276405 A1 | 11/2007 | Heubner et al. | |
| 2008/0255620 A1 | 10/2008 | Strauss et al. | |
| 2009/0069851 A1 | 3/2009 | Gillard et al. | |
| 2009/0198277 A1 | 8/2009 | Gordon | |
| 2010/0305618 A1 | 12/2010 | Kay et al. | |
| 2011/0093018 A1 | 4/2011 | Prasad et al. | |
| 2011/0106182 A1 | 5/2011 | Reisberg | |
| 2013/0165933 A1 | 6/2013 | Gephart | |

* cited by examiner

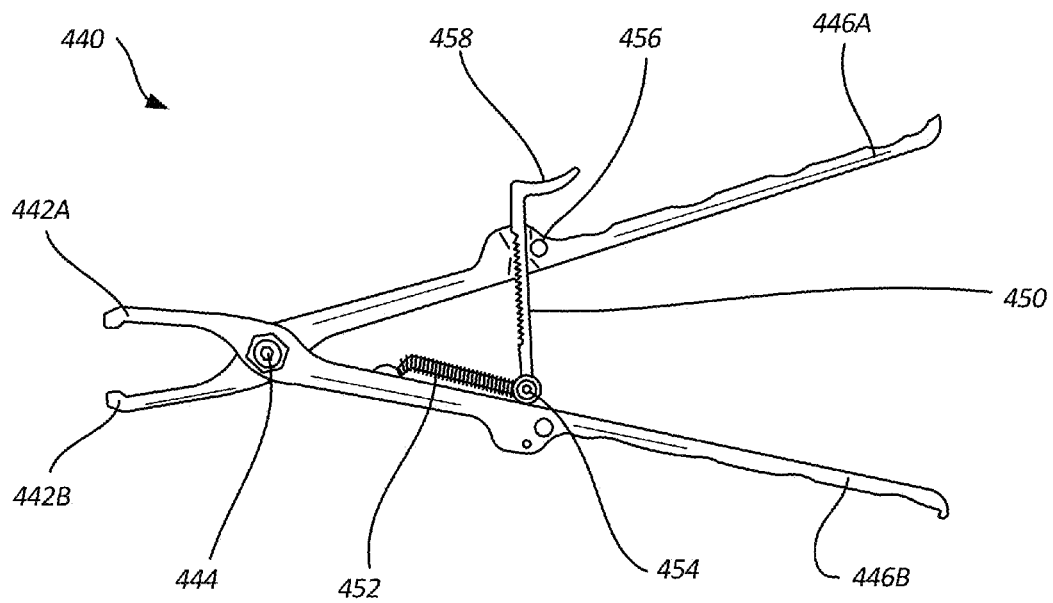
FIG. 29A
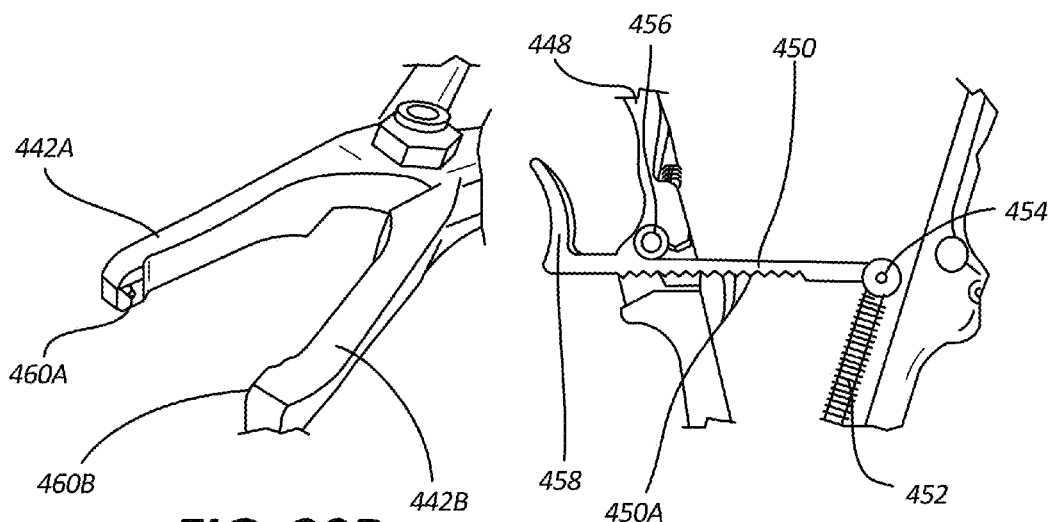
FIG. 29B  FIG. 29C

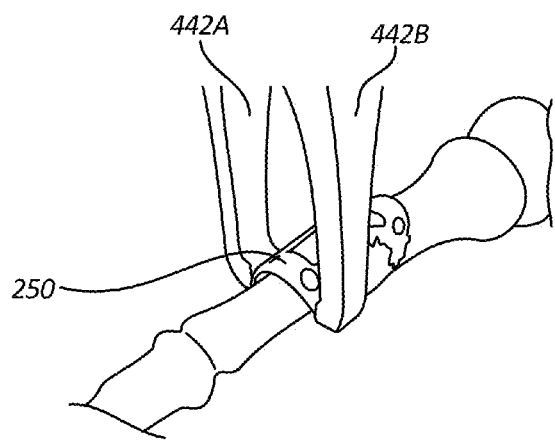
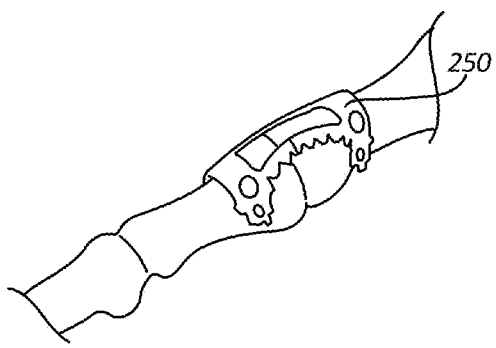
FIG. 32E        FIG. 32F
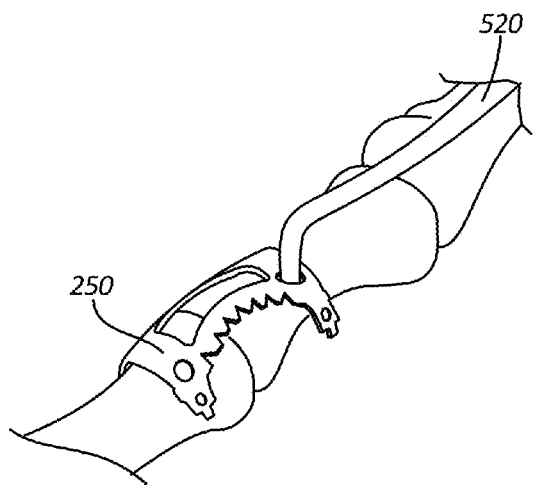
FIG. 33

BONE FUSION/FIXATION DEVICE AND RELATED SYSTEMS AND METHODS

CROSS-REFERENCE TO RELATED APPLICATION(S)

This application claims the benefit under 35 U.S.C. § 371 to International PCT Patent Application No. PCT/US15/18111, filed on Feb. 27, 2015, which claims priority to U.S. Provisional Application 61/945,511, filed Feb. 27, 2014 and entitled "Digital Deformity Fusion/Fixation Device and Related Methods," which is hereby incorporated herein by reference in its entirety.

FIELD OF THE INVENTION

The various embodiments disclosed herein relate to bone fixation or fusion devices, including intramedullary fixation or fusion devices that are implanted around the target bone. In addition, other embodiments relate to implantation devices that can be used to implant or position the bone fixation or fusion devices.

BACKGROUND OF THE INVENTION

Digital arthrodesis of the foot is a common surgical procedure for correction of acquired or congenital digital deformities, including, for example, hammertoe, mallet toe deformities, and similarly encountered foot maladies affecting or involving the digits (toes).

Historically, the involved digit(s) and respective joints are corrected via a stepwise reduction using, for example, a specific joint resection arthoplasty, (cutting a small amount of articular cartilage and bone to straighten and maintain flexibility of the involved digit) or a specific joint arthrodesis (fusion or permanent stiffening of the joint in a corrected neutral position). Prior to the creation of the various embodiments disclosed herein, the "gold standard" of affixing and imparting mechanical stability to an intended digital arthrodesis has been the application of a single intramedullary positioned standard sized Kirschner wire ("K-wire"), which is routinely exposed externally to the distal tip of the involved digit. For example, FIG. 1A depicts a K-wire positioned in an affected digit. Many surgeons have employed the K-wire for the express purpose of providing stability to the intended arthrodesis site and/or maintaining, stabilizing, and/or directly reducing concurrent metatarsophalngeal joint contracture associated with digital deformity.

Disadvantages of standard K-wire fixation include the defined requirement of removal, migration, bending, or breaking of the "K-wire," loss of fixation and/or loss of stability at the intended arthrodesis site, pin tract site irritation, inflammation, pain, and/or development of infection, including deep infection, and the routine external exposure of the K-wire, which is recognized to leave patients and physicians dissatisfied. More specifically, K-wire fixation remains external to the distal aspect of the digit, resulting in a variety of potential problems, including wound complications, limitation of ambulation, and secondary events. Furthermore, following K-wire removal, the potential loss of stability at the intended arthrodesis site can be related to recurrence of deformity, fibrous union, non-union, and pain, as well as failure to gain lasting correction of the deformity.

Newer known intra-medullary devices—solid and cannnulated designs—are commercially available as an alternative fixation device to traditional K-wire fixation, offering completely internal placement. FIG. 1B depicts one embodiment of solid intra-medullary devices. These newer devices are intended to afford a greater degree of intramedullary fixation and stability to the intended arthrodesis site and obviate the need for an exposed intra-medullary fixation device. (i.e. "K-wire" fixation.)

Complications of emerging solid and/or cannulated intramedullary devices are well established, including failure to impart stability, loss of stability, loss of fixation, breakage of device, fracture of adjacent cortical bone, device loosening, osteolysis, handling and storage constraints due to metallurgy properties, inventory control dissatifiers, cost, difficulty in removal, bone loss, secondary procedures, and complications salvaged via explanation, revisional arthrodesis, bone grafting considerations, adjacent digit syndactyly and/or digital amputation. Further, few of the newer intramedullar technologies are compatible and approved (via 510K clearance) to be used concurrently with Kirschner wire fixation.

There is a need in the art for an improved extramedullary device designed specifically for the intended arthrodesis of a digital arthrodesis of the foot or hand.

BRIEF SUMMARY OF THE INVENTION

Discussed herein are various bone fixation or fusion devices and related systems and methods.

In Example 1, a bone fixation device comprises at least one spine, at least two distal arms extending from a distal end of the at least one spine, least two proximal arms extending from a proximal end of the at least one spine, and at least one opening defined in the bone fixation device, wherein the opening is sized and shaped to receive a portion of an implantation tool. Each of the at least two distal arms comprises at least one distal bone tine, and the at least two distal arms are configured to be positionable around a bone. Each of the at least two proximal arms comprises at least one proximal bone tine, and the at least two proximal arms are configured to be positionable around a bone.

Example 2 relates to the bone fixation device according to Example 1, wherein the at least one spine comprises a first spine and a second spine.

Example 3 relates to the bone fixation device according to Example 2, wherein the first and second spines comprise notches defined along a length of each of the first and second spines.

Example 4 relates to the bone fixation device according to Example 2, wherein the first and second spines are curvy spines.

Example 5 relates to the bone fixation device according to Example 1, wherein the opening comprises internal threads, wherein the internal threads are configured to receive external threads of the implantation tool.

Example 6 relates to the bone fixation device according to Example 1, wherein the at least one opening comprises at least four openings, wherein each of the at least two distal arms and the at least two proximal arms defines at least one of the at least four opening.

Example 7 relates to the bone fixation device according to Example 1, wherein the at least one opening comprises at least two openings, wherein the at least one spine defines the at least two openings.

Example 8 relates to the bone fixation device according to Example 1, further comprising at least one arm deformation opening defined in at least one of the at least two distal arms and the at least two proximal arms, wherein the at least one arm deformation opening is configured to facilitate deformation of the at least one of the at least two distal arms and the at least two proximal arms.

Example 9 relates to the bone fixation device according to Example 1, wherein the at least one spine comprises a joint or fracture site indicator line.

Example 10 relates to the bone fixation device according to Example 1, further comprising at least one arm deformation notch defined in at least one of the at least two distal arms and the at least two proximal arms, wherein the at least one arm deformation notch is configured to facilitate deformation of the at least one of the at least two distal arms and the at least two proximal arms.

In Example 11, a bone fixation device comprises a first spine comprising a first curved inner edge and a first outer edge comprising a plurality of notches, a second spine comprising a second curved inner edge and a second outer edge comprising a plurality of notches, at least two distal arms extending from a distal end of the first and second spines, at least two proximal arms extending from a proximal end of the first and second spines, at least one tool interface opening defined in the bone fixation device, and at least one arm deformation feature defined in the bone fixation device. Each of the at least two distal arms comprises at least one distal bone tine and the at least two distal arms are configured to be positionable around a bone. Each of the at least two proximal arms comprises at least one proximal bone tine and the at least two proximal arms are configured to be positionable around a bone. The at least one tool interface opening is sized and shaped to receive a portion of an implantation tool. The at least one arm deformation feature is configured to facilitate deformation of at least one of the at least two distal arms and the at least two proximal arms.

Example 12 relates to the bone fixation device according to Example 11, wherein the at least one tool interface opening comprises internal threads, wherein the internal threads are configured to receive external threads of the implantation tool.

Example 13 relates to the bone fixation device according to Example 11, wherein the at least one tool interface opening comprises at least four openings, wherein each of the at least two distal arms and the at least two proximal arms defines at least one of the at least four tool interface openings.

Example 14 relates to the bone fixation device according to Example 11, wherein the at least one arm deformation feature comprises an opening or a notch.

Example 15 relates to the bone fixation device according to Example 11, wherein the first and second spines comprise a joint or fracture site indicator line.

In Example 16, a bone fixation device comprises at least one spine, at least two distal arms extending from a distal end of the at least one spine, and at least two proximal arms extending from a proximal end of the at least one spine. Each of the at least two distal arms comprises at least one distal deformation control opening and the at least two distal arms are configured to be positionable around a bone. Each of the at least two proximal arms comprises at least one proximal deformation control opening, and the at least two proximal arms are configured to be positionable around a bone. The distal and proximal deformation control openings are configured to facilitate deformation of the at least two distal arms and the at least two proximal arms.

Example 17 relates to the bone fixation device according to Example 16, wherein the distal and proximal deformation control openings are configured to provide for deformation of the at least two distal arms and the at least two proximal arms in a desired direction.

Example 18 relates to the bone fixation device according to Example 16, wherein the distal and proximal deformation control openings are configured to provide for local bend radii of the distal and proximal arms that differ from local bend radii of the distal and proximal arms in the absence of the deformation control openings.

Example 19 relates to the bone fixation device according to Example 16, wherein each of the at least two distal arms and the at least two proximal arms comprise at least one bone tine, wherein each at least one bone tines is positioned at a radius of curvature that is more acute than a radii of curvature within the at least two distal arms and the at least two proximal arms.

Example 20 relates to the bone fixation device according to Example 16, wherein each of the at least two distal arms and the at least two proximal arms comprises a first bend radius imparted around the distal and proximal deformation control openings, a second bend radius imparted on the arm between the deformation control opening and a bone tine, and a third bend radius imparted on the bone tine.

Example 21 relates to the bone fixation device according to Example 20, wherein the first, second, and third bend radii are non-circular in cross-section.

In Example 22, a bone fixation kit comprises a bone fixation device, a support block on which the bone fixation device can be disposed such that the at least one spine, the first and second distal arms, and the first and second proximal arms conform to a shape of the support block, and an implantation tool that is coupleable with the first and second distal arms and the first and second proximal arms to remove the bone fixation device from the support block. The bone fixation device comprises at least one spine, first and second distal arms extending from a distal end of the at least one spine, each of the first and second distal arms comprising at least one distal bone tine, and first and second proximal arms extending from a proximal end of the at least one spine, each of the first and second proximal arms comprising at least one proximal bone tine.

In Example 23, a bone fixation method comprises providing a bone fixation device, positioning the first and second distal arms around a first target bone site, crimping the first and second distal arms around the first target bone site with an implantation tool such that the at least one distal bone tine is embedded in the first target bone site, positioning the first and second proximal arms around a second target bone site, and crimping the first and second proximal arms around the second target bone site with the implantation tool such that the at least one proximal bone tine is embedded in the second target bone site. The bone fixation device comprises at least one spine, first and second distal arms extending from a distal end of the at least one spine, each of the first and second distal arms comprising at least one distal bone tine, and first and second proximal arms extending from a proximal end of the at least one spine, each of the first and second proximal arms comprising at least one proximal bone tine.

Example 24 relates to the bone fixation method according to Example 23, further comprising deforming the at least one spine to replicate a natural bend at the first and second target bone sites.

Example 25 relates to the bone fixation method according to Example 23, wherein first target bone site comprises a first bone and the second target bone site comprises a second bone, wherein the bone fixation device is positioned across a joint between the first and second bones.

Example 26 relates to the bone fixation method according to Example 23, wherein the bone fixation device further comprises at least first and second distal tool interface openings defined in the first and second distal arms and at least first and second proximal tool interface openings defined in the first and second proximal arms, wherein the crimping the first and second distal arms further comprises coupling the implantation tool to the first and second distal tool interface openings, and wherein the crimping the first and second proximal arms further comprises coupling the implantation tool to the first and second proximal tool interface openings.

Example 27 relates to the bone fixation method according to Example 23, further comprising coupling the implantation tool to at least first and second distal tool interface openings defined in the first and second distal arms prior to positioning the first and second distal arms around the first target bone site and coupling the implantation tool to at least first and second proximal tool interface openings defined in the first and second proximal arms prior to positioning the first and second proximal arms around the second target bone site.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 5B is a perspective view of the fixation/fusion device of FIG. 5A in which an advancement tool has been removed and the device is implanted, according to one embodiment.

FIG. 29A is a front view of a implantation device, according to one embodiment.

FIG. 29B is an expanded perspective view of the jaw of the implantation device of FIG. 29A.

FIG. 29C is an expanded front view of the ratchet mechanism of the implantation device of FIG. 29A.

FIG. 32E is a perspective view of the application tool crimping the opposite end of the fixation/fusion device of FIG. 32A in place at the target bone site, according to one embodiment.

FIG. 32F is a perspective view of the fixation/fusion device of FIG. 32A implanted at the target bone site, according to one embodiment.

FIG. 33 is a perspective view of the fixation/fusion device of FIG. 32A being removed with a removal tool, according to one embodiment.

DETAILED DESCRIPTION

The various embodiments disclosed and contemplated herein relate to anatomic, site-specific extra-medullary fixation and/or fusion devices (and related systems and methods) designed to achieve satisfactory mechanical and clinical benefit over traditional K-wire fixation and emerging new solid and/or cannulated intramedullary fixation technologies. Certain implementations are designed specifically for digital arthrodesis of the foot (or hand). More specifically, the various embodiments relate to a system comprising an anatomically specific extramedullary digital fixation device and a related application tool.

Figure 1A:
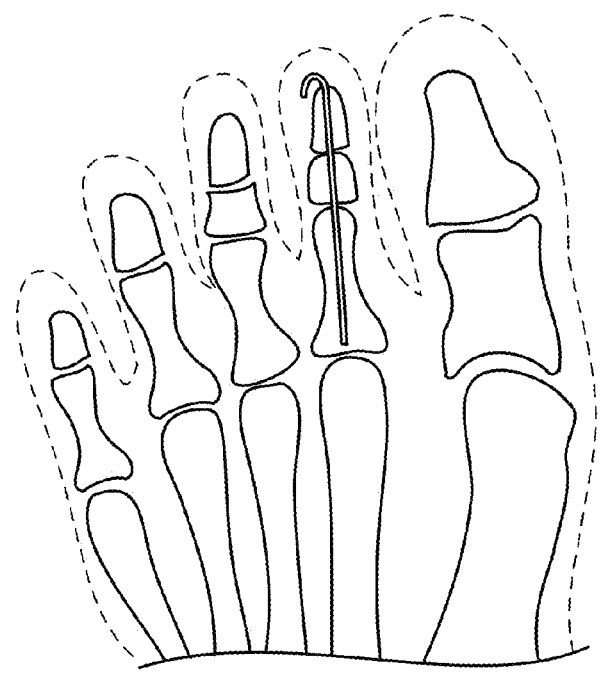
FIG. 1A is a front view of an X-ray image of a known K-wire device positioned in an affected digit.
Figure 1B:
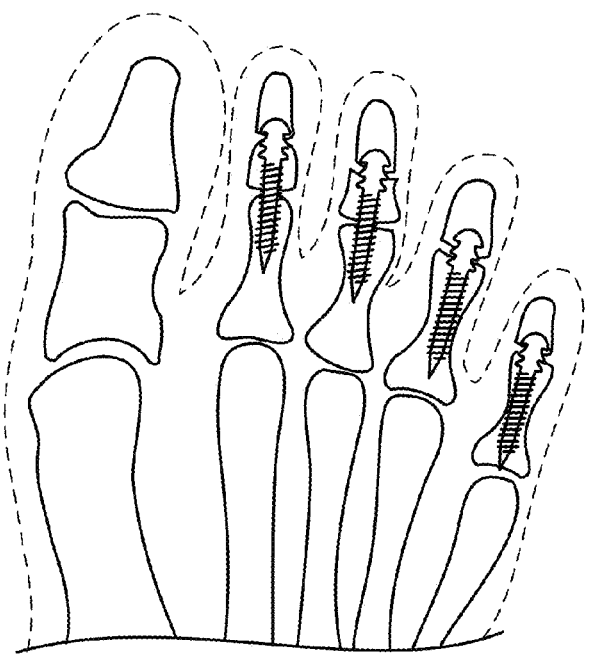
FIG. 1B is a front view of an X-ray image of known intra-medullary devices positioned in affected digits.
Figure 2A:
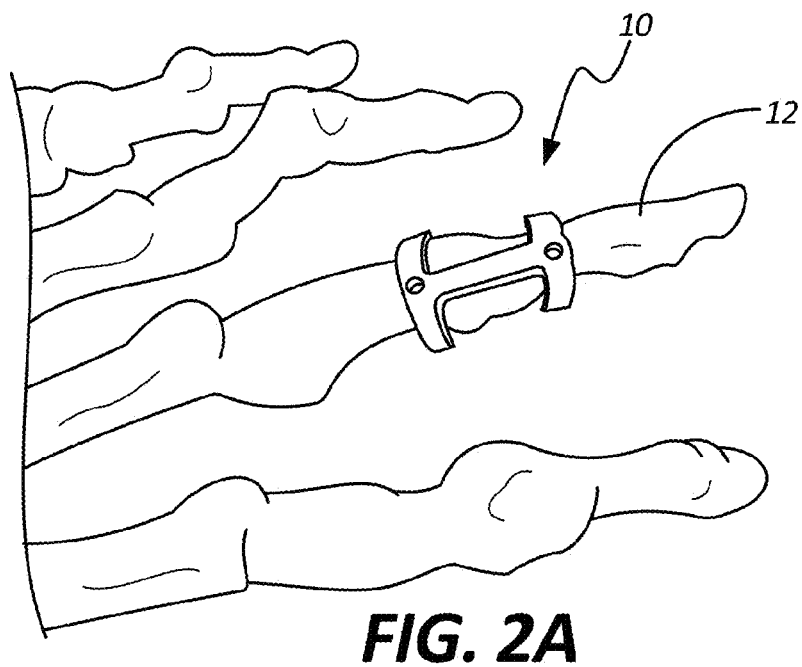
FIG. 2A is a top view of a fusion or fixation device affixed to a target site on a digit, according to one embodiment.
Figure 2B:
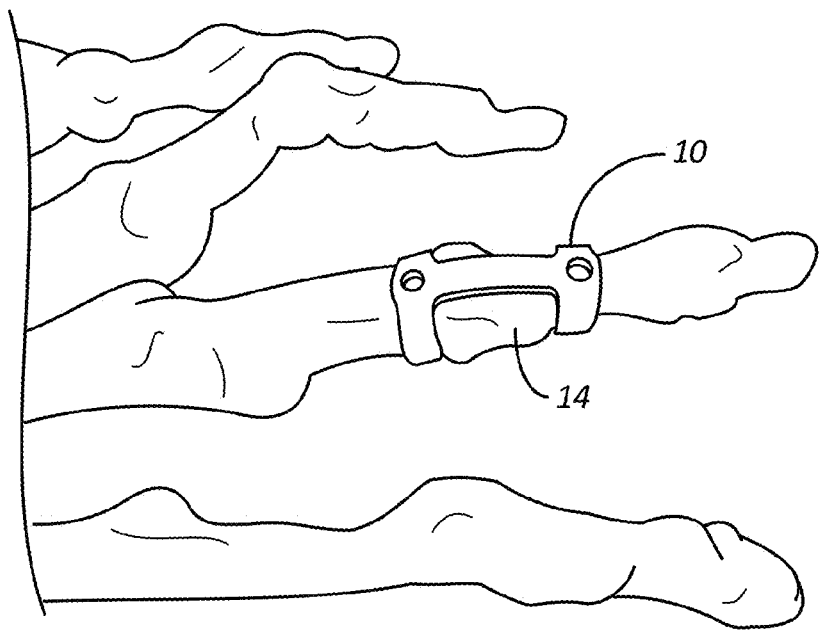
FIG. 2B is a perspective view of the fusion or fixation device of FIG. 2A.
Figure 2C:
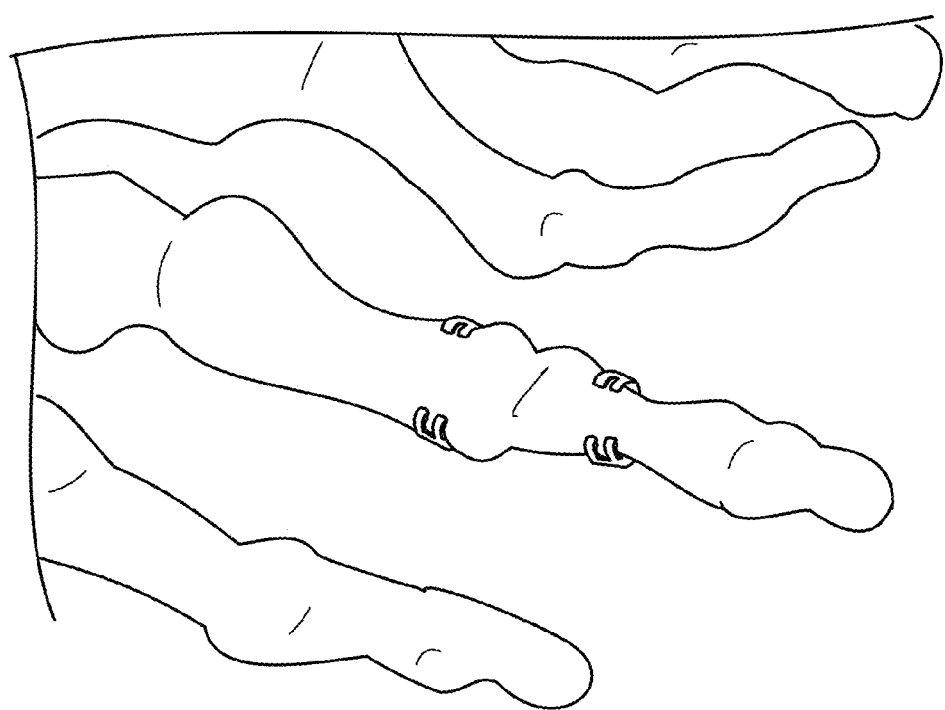
FIG. 2C is an underside view of the fusion or fixation device of FIG. 2A.

FIGS. 2A-2C depict one specific exemplary embodiment of a fusion or fixation device 10 affixed to a target site on a digit 12. Each of the various embodiments disclosed herein can be affixed to the target site as the sole fusion or fixation device. That is, any of these embodiments can be used on their own, without any other known devices. Alternatively, the various embodiments can also be used concurrently with "K-wire" fixation devices or other known devices per clinical need and/or surgeon preference. That is, the various embodiments are configured to be capable of and compatible with the concurrent use of a K-Wire. Surgeons may elect to adjunctively apply such "K-wire" adjunct to stabilize and control the position of the digit at the metatarsal philangeal joint level following a step-wise surgical release and correction to the proximal phalangeal joint contracture and deformity. The various implementations disclosed herein allow such adjunctive use. In contrast, other known technologies as described herein cannot be used in combination with or concurrently with a K-wire.

The various embodiments disclosed herein relate to a device of enhanced stability positioned over/against the intended arthrodesis site over time. In FIGS. 2A-2C, the device 10 is positioned across the joint 14 on digit 12, thereby causing fusion of the two bones at the joint 14. The embodiments disclosed herein, including the exemplary device 10, relate to anatomically specific extra-medullary fixation and/or fusion devices that are affixed to the desired small joint arthrodesis and positioned over portions of each of the related phalanx segments and "crimped" or otherwise affixed thereto, thereby providing an entirely externally-based fixation method construct which provides satisfactory mechanical support to the intended arthrodesis site. In addition, the extra-medullar device embodiments disclosed herein allow for easier removal of such devices in comparison to the known intramedullar designs.

FIGS. 3A-3G and 4 depict one embodiment of an extramedullary fixation/fusion device 10. The device 10 has a spine 20 coupled to a pair of distal arms 22A, 22B at the distal end and a pair of proximal arms 24A, 24B at the proximal end. In this implementation, the spine 20 also has a distal tine 26 and a proximal tine 28. Similarly, the distal arms 22A, 22B each have a tine 30A, 30B, and the proximal arms 24A, 24B also each have a tine 32A, 32B.

In one embodiment, the device 10 is made of an appropriate semi-rigid, deformable material. In certain examples, the device 10 is made from any of a variety of metal alloys, including, for example, medical grade stainless steel, titanium, or other similar materials.

Figure 3A:
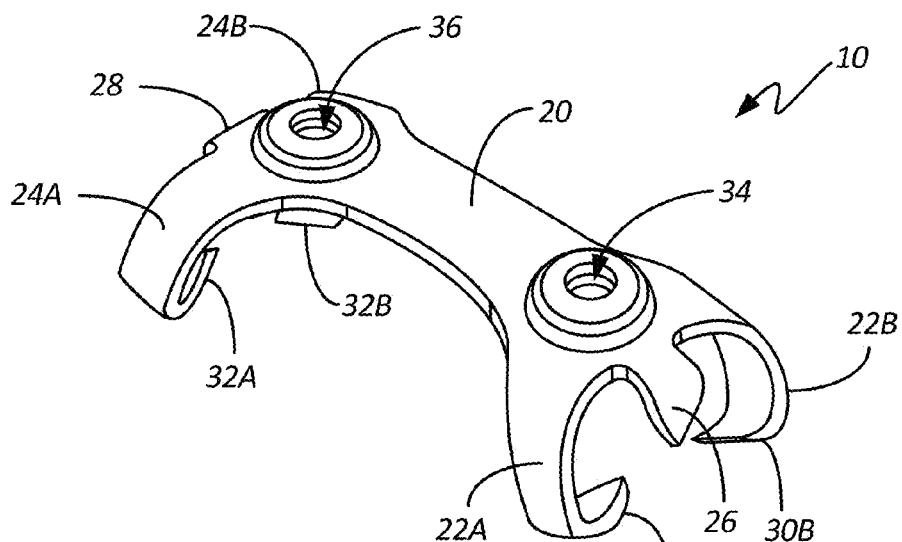
FIG. 3A is a perspective view of a fixation/fusion device, according to another embodiment.
Figure 3B:
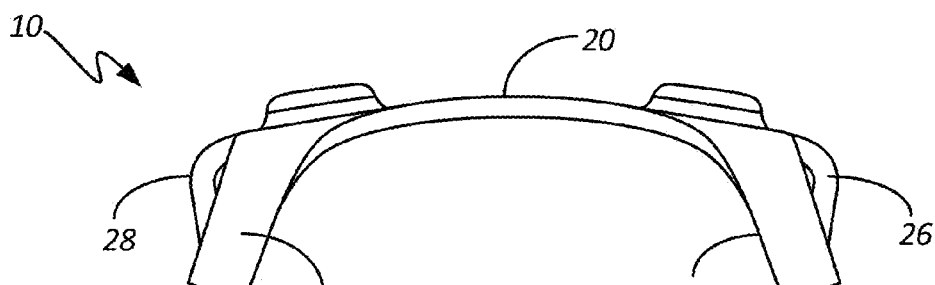
FIG. 3B is a side view of the fixation/fusion device of FIG. 3A.
Figure 3C:
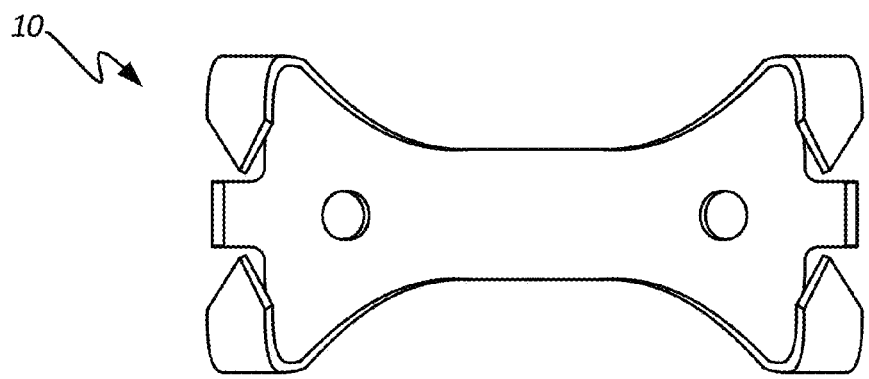
FIG. 3C is an underside view of the fixation/fusion device of FIG. 3A.
Figure 3D:
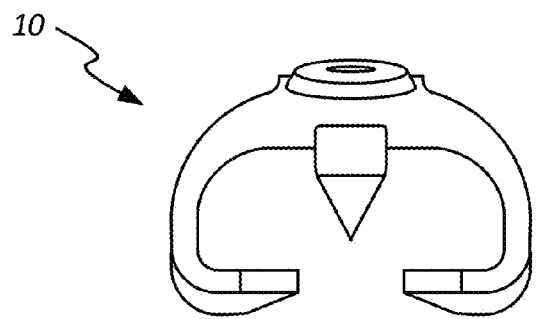
FIG. 3D is an end view of the fixation/fusion device of FIG. 3A.

In the various embodiments disclosed and contemplated herein, including any embodiments described throughout this application, the device can have a thickness ranging from at least about 0.1 mm to about 2 mm. The length of the device (distance between the arm tines as best shown in FIGS. 3B and 3C as the distance between tine 32A and tine 30A) ranges from about 5 mm to about 10 cm. The width of the device between the arms (as best shown in FIG. 3D as the distance between the distal ends of arms 22A and 22B) ranges from about 1 mm to about 20 mm. The width of the spine (best shown in FIG. 3C) ranges from about 1 mm to about 10 mm, and the width of an arm (as shown for example in FIG. 3B) ranges from about 1 mm to about 10 mm.

In this implementation, the spine 20 also has two mounting features 34, 36. More specifically, the mounting features in this embodiment are two threaded openings 34, 36 configured to receive an application tool, as discussed in further detail below.

Figure 3E:
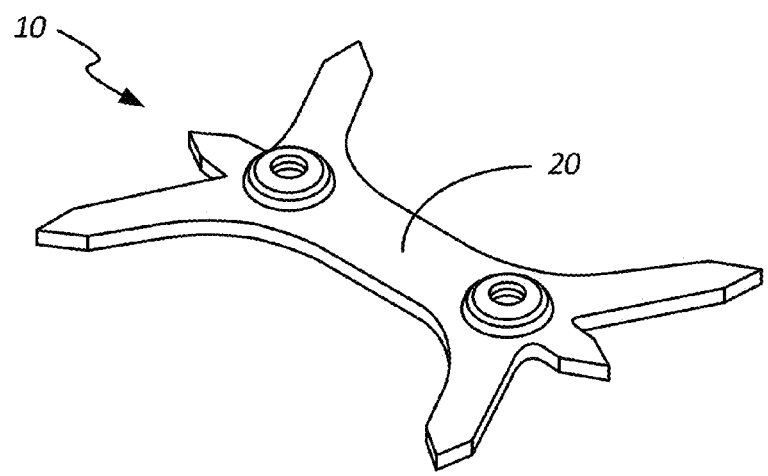
FIG. 3E is an perspective view of the fixation/fusion device of FIG. 3A prior to being formed into the desired shape.
Figure 3F:
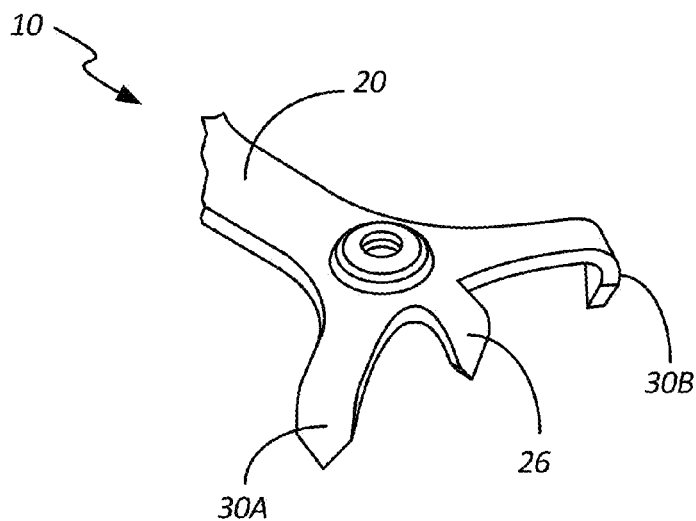
FIG. 3F is a perspective view of the fixation/fusion device of FIG. 3A in which formation of the desired shape has begun.
Figure 3G:
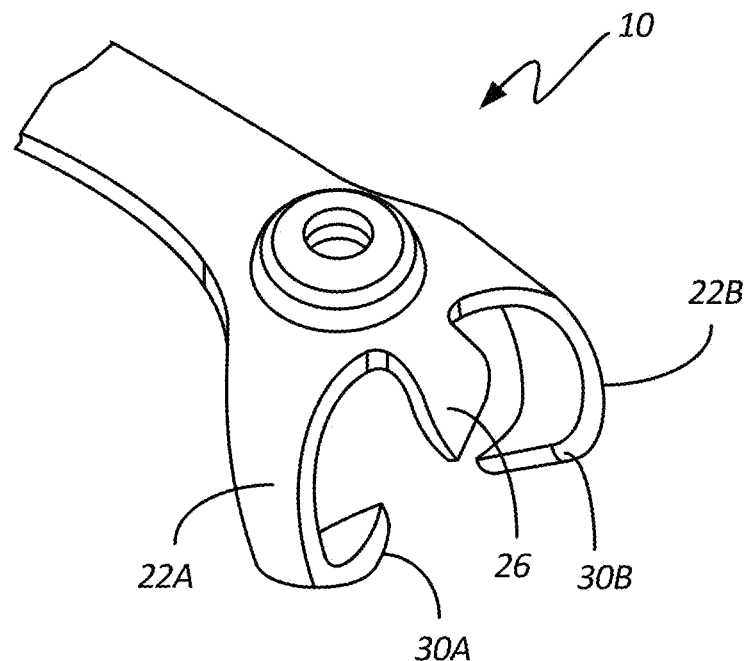
FIG. 3G is a perspective view of the fixation/fusion device of FIG. 3A in which formation of the desired shape is complete.

As best shown in FIGS. 3E, 3F, and 3G, in accordance with one embodiment, the device 10 can be cut from a sheet of metal (or other material) into a flat piece as shown in FIG. 3E that is subsequently formed into the desired shape for the device 10. In one embodiment, the specific configuration and footprint of the device 10, including the length, width, geometry and thickness, is based upon the intended arthrodesis site morphology and anatomic restraints. That is, the specific size and dimensions of the device 10 can be determined by the size and dimensions of the target site.

In one specific embodiment, the device 10 can be formed from sheet metal. More specifically, it can be cut or stamped into the configuration of FIG. 3E using any one of a variety of methods, including, for example, laser cutting, edm, die cutting, or any other known method.

Alternatively, it is understood that the flat piece could also be formed in any known way.

Any bends or desired deformations associated with the tines, arms, and/or spine can be introduced during the stamping process or post cutting using a variety of known forming methods such as, for example, stamping, fourslide bending, bending presses, etc. Alternatively, some or all of the bends or deformations can be introduced in the application process (during the fixation/implantation procedure) instead of in the manufacturing process.

In a further alternative, the arms and/or tine can be manufactured separately from the sheet metal or pins and attached by any known attachment method, such as welding.

Figure 4:
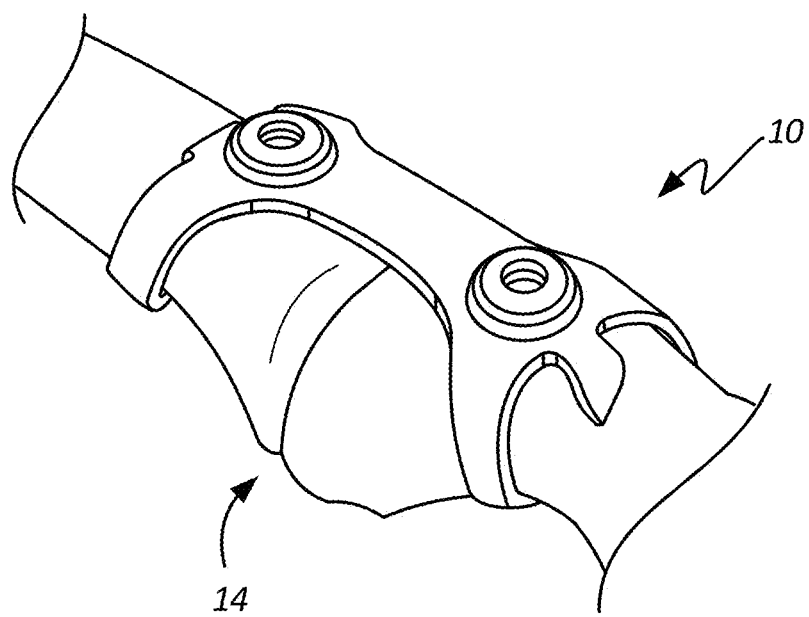
FIG. 4 is a perspective view of a fixation/fusion device implanted or fixed in place across a joint, according to one embodiment.

Once the flat piece of FIG. 3E is formed, the tines (such as tines 26, 30A, and 30B as shown in FIG. 3F) are formed by bending the tines into their desired configuration as shown. According to one implementation, due to the amount of force required, the tines (such as tines 26, 30A, and 30B) are bent as desired during the manufacturing process (rather than being bent in the operating area immediately prior to or during a procedure). The arms (such as arms 22A, 22B as shown in FIG. 3G) can then be bent into their desired configuration. This can be accomplished during the manufacturing process or anytime thereafter, including during the procedure as described in further detail below. Further, the spine 20 can also be bent into a curved configuration as best shown in FIG. 3B, and this can also occur at anytime (from the manufacturing process forward). FIG. 4 depicts the device 10 implanted or fixed in place across a joint 14.

Figure 5A:
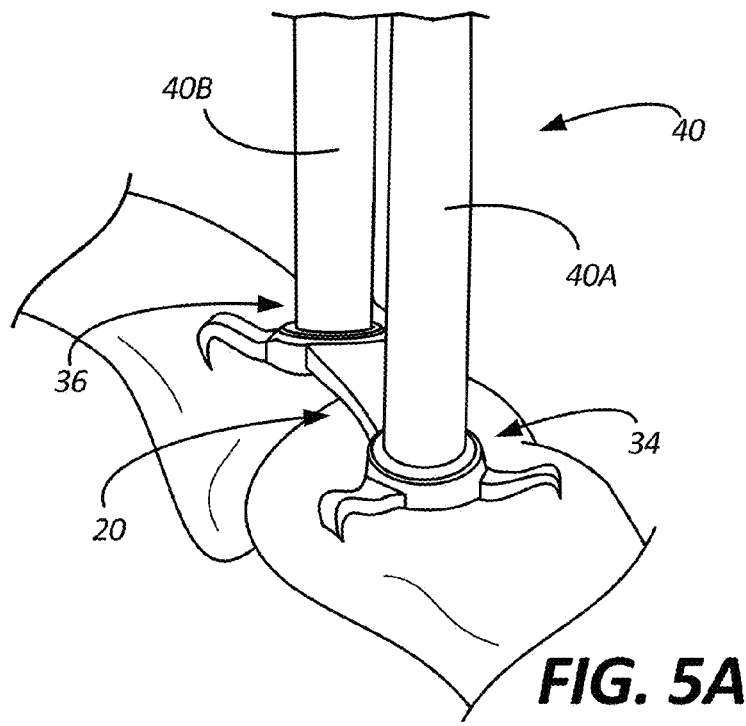
FIG. 5A is a perspective view of a fixation/fusion device coupled to an application tool for purposes of implantation, according to one embodiment.

In use in accordance with one embodiment, the device 10 (and any of the device embodiments disclosed or contemplated herein) can be placed onto, implanted, or fixed on the desired target site according to the following steps. As shown in FIG. 5A, the application tool 40 is coupled to the mounting features 34, 36 of the device 10. More specifically, in this particular implementation, the tool 40 is made up of two application rods or bars 40A, 40B that are threadably coupled to the mounting features 34, 36 such that the rods 40A, 40B are coupled to the device 10. Once the target site is surgically accessed and the digit(s) and respective joints have been prepared to facilitate joint fusion, the tool 40 can, in certain embodiments, be used to assist in positioning the device 10 as desired at the target site (such as a proximal phalangeal joint, for example).

Figure 5B:
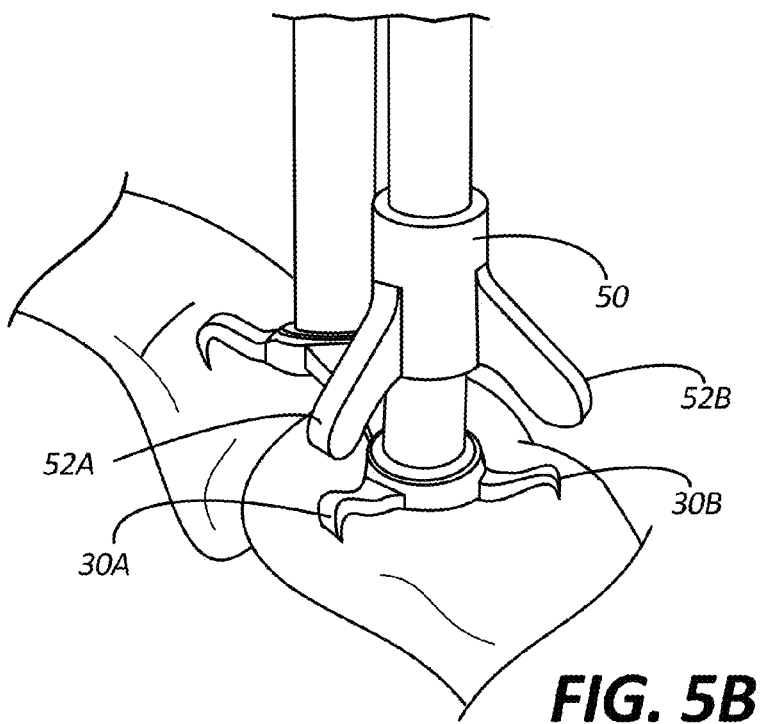
FIG. 5B is a perspective view of the fixation/fusion device of FIG. 5A in which an advancement tool is being advanced toward the fixation/fusion device, according to one embodiment.
Figure 5C:
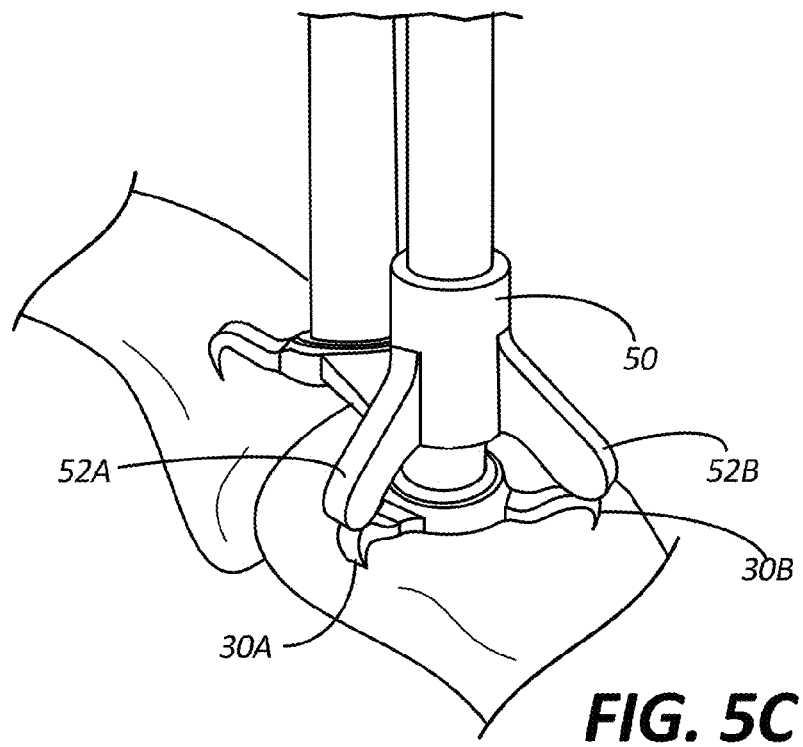
FIG. 5C is a perspective view of the fixation/fusion device of FIG. 5A in which an advancement tool is in contact with the fixation/fusion device, according to one embodiment.

An advancement tool 50 is then advanced over one of the rods 40A as shown in FIG. 5B. The advancement tool 50 has two protrusions 52A, 52B corresponding to the tines on the device (such as, for example, the distal tines 30A, 30B of device 10). Alternatively, the tool 50 can have any appropriate number of protrusions to match the number of tines. The tool 50 is then advanced distally along the rod 40A until the protrusions 52A, 52B are in contact with the tines 30A, 30B, as best shown in FIG. 5C.

Figure 5D:
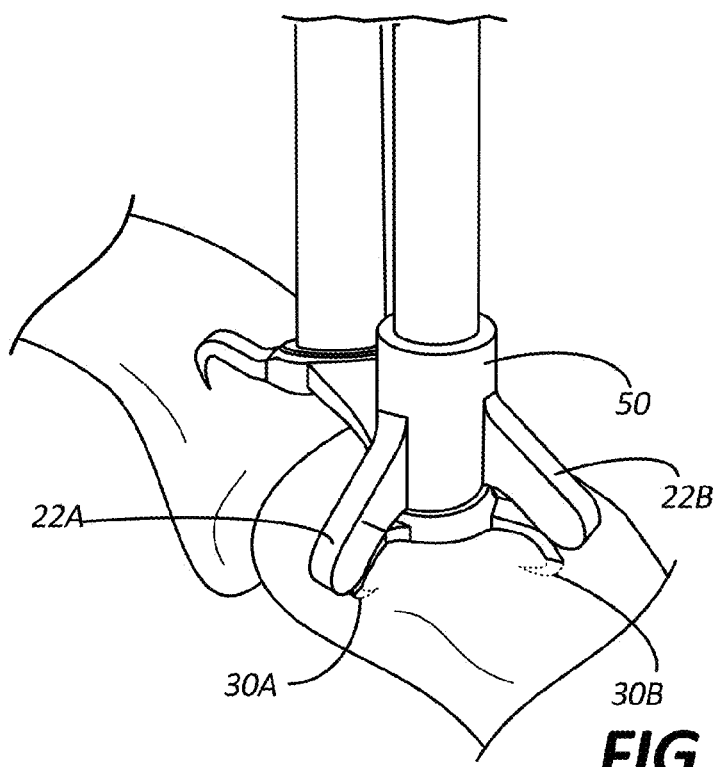
FIG. 5D is a perspective view of the fixation/fusion device of FIG. 5A in which an advancement tool urges the tines of the fixation/fusion device into the bone, according to one embodiment.
Figure 5E:
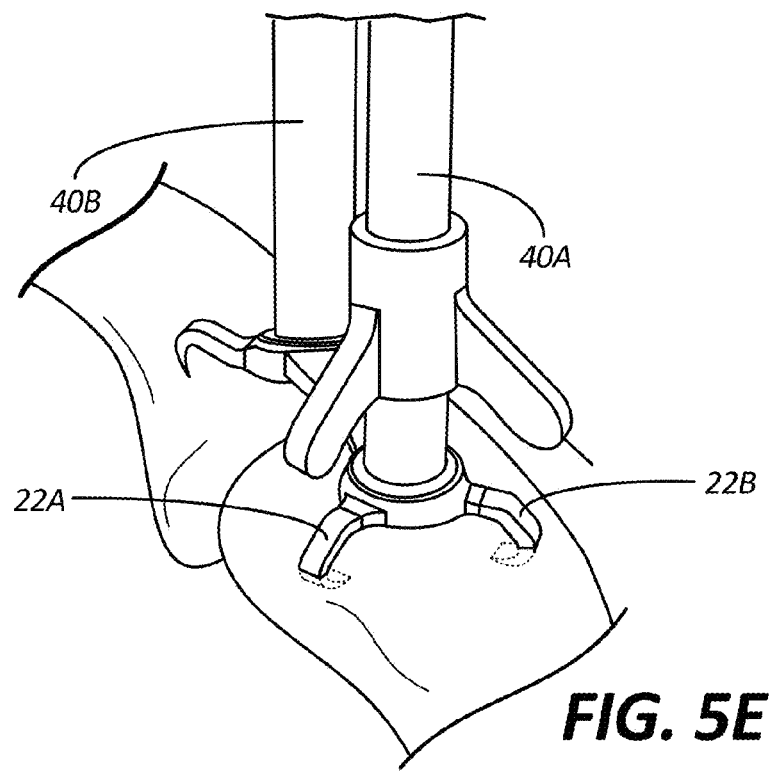
FIG. 5E is a perspective view of the fixation/fusion device of FIG. 5A in which the advancement tool is being removed, according to one embodiment.
Figure 5F:
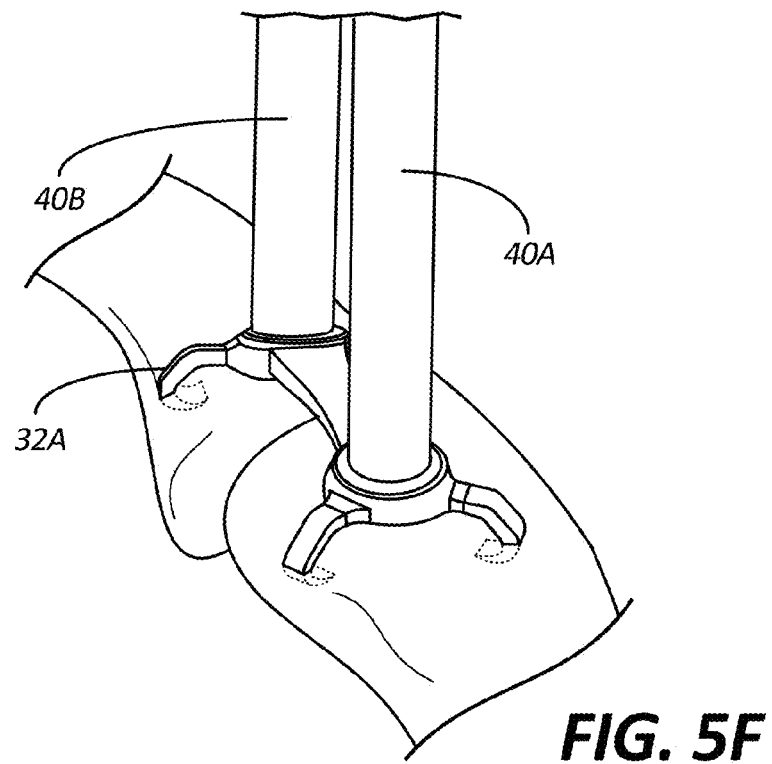
FIG. 5F is a perspective view of the fixation/fusion device of FIG. 5A in which the tines of the fixation/fusion device are embedded into the bone, according to one embodiment.
Figure 5G:
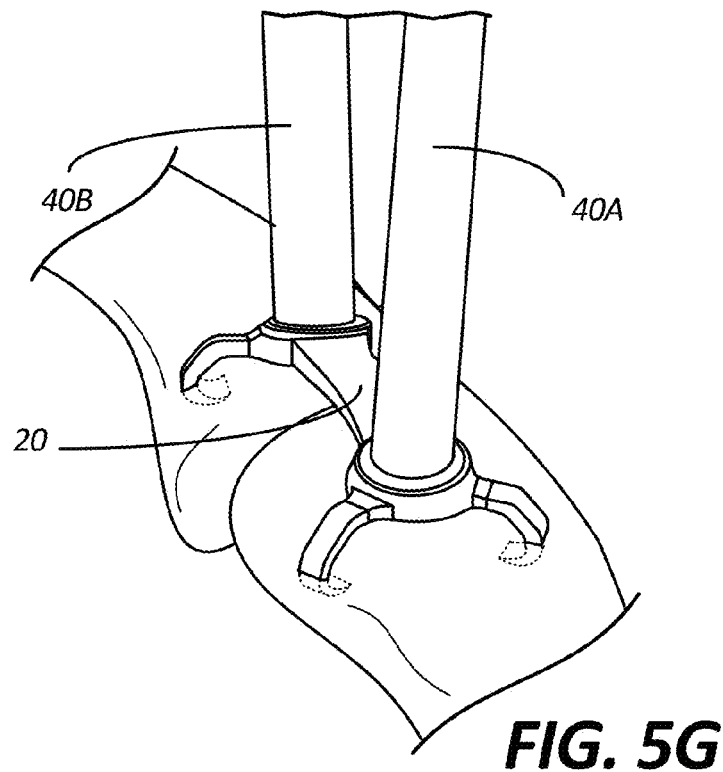
FIG. 5G is a perspective view of the fixation/fusion device of FIG. 5A in which the two rods of the advancement tool are urged apart to bend the device, according to one embodiment.
Figure 5H:
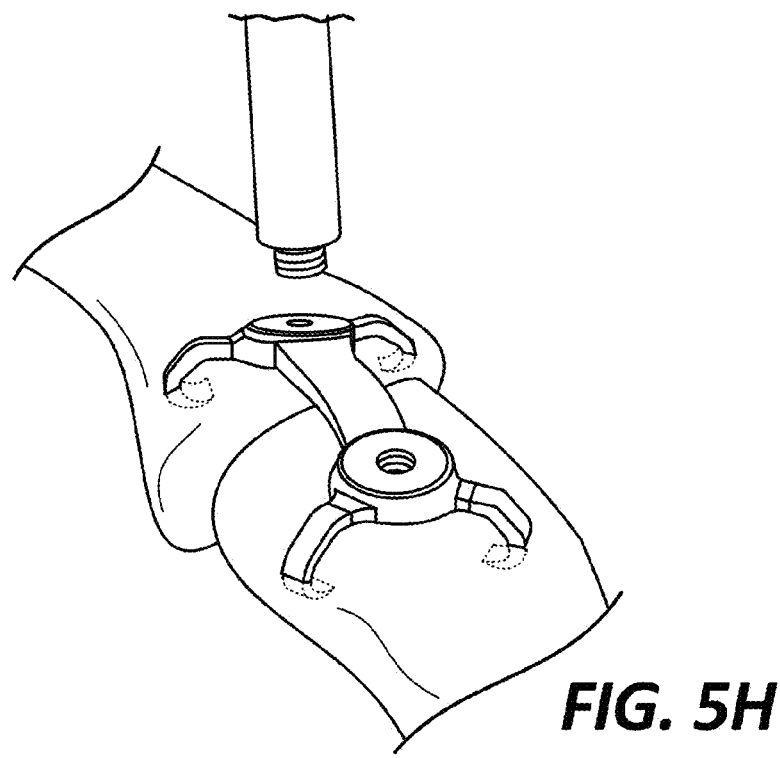
FIG. 5H is a perspective view of the fixation/fusion device of FIG. 5A in which the advancement tool is being removed, according to one embodiment.
Figure 51:
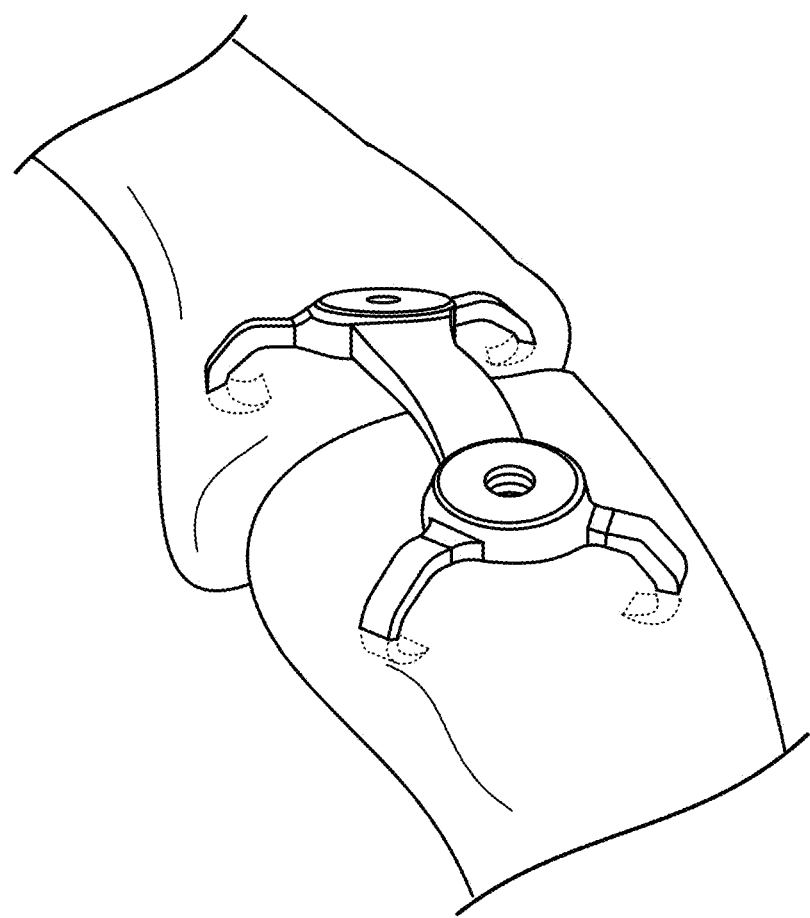
Figure 6A:
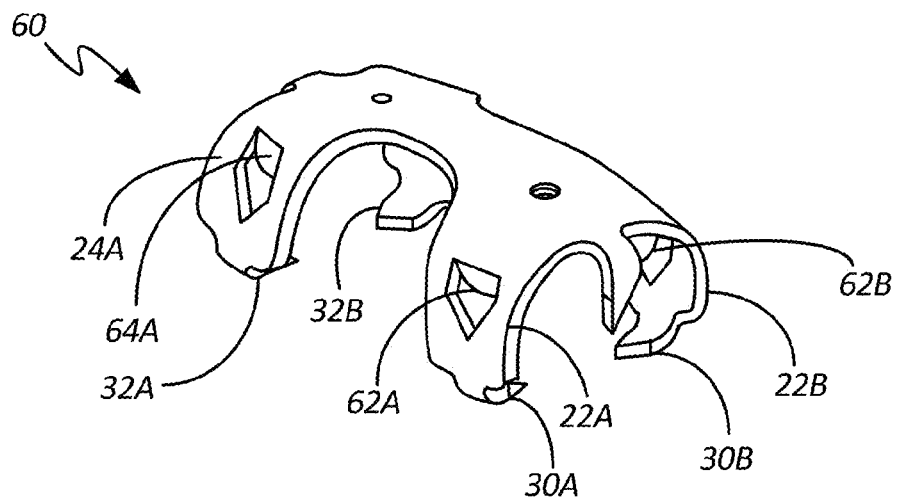
FIG. 6A is a perspective view of a fixation/fusion device, according to another embodiment.
Figure 6B:
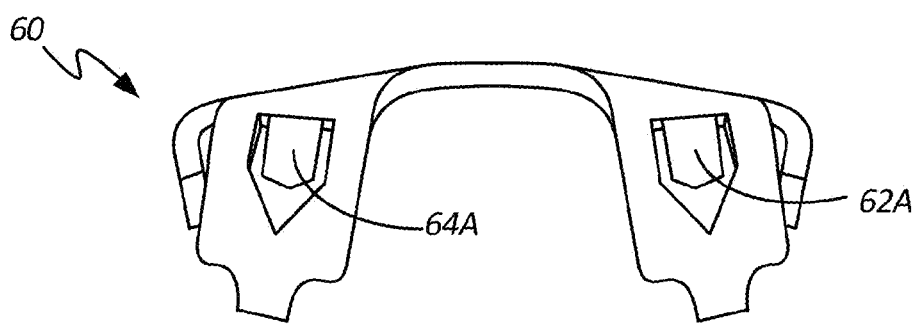
FIG. 6B is a side view of the fixation/fusion device of FIG. 6A.
Figure 6C:
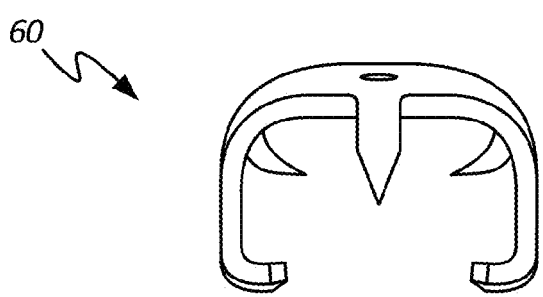
FIG. 6C is an end view of the fixation/fusion device of FIG. 6A.
Figure 6D:
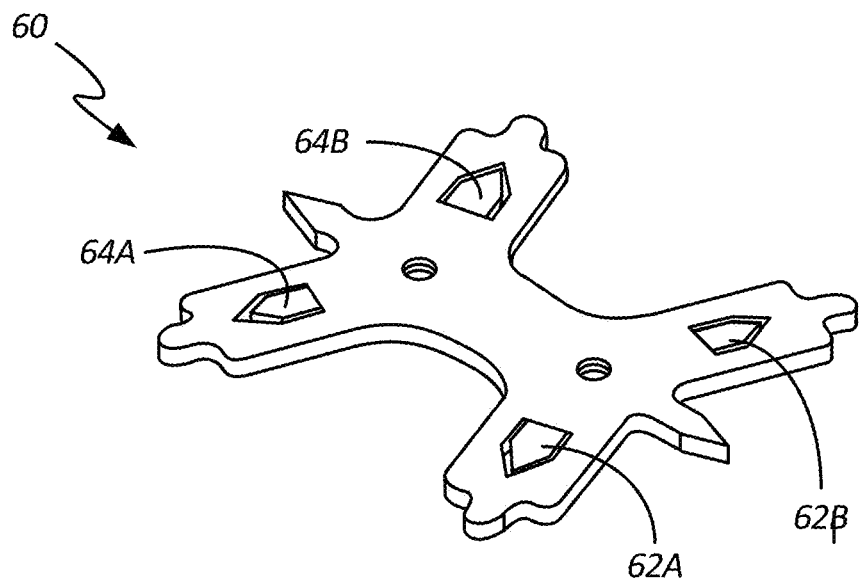
FIG. 6D is an perspective view of the fixation/fusion device of FIG. 6A prior to being formed into the desired shape.

The tool 50 is then urged distally along the rod 40A such that the protrusions 52A, 52B urge the tines 30A, 30B into the cortical bone as shown in FIG. 5D. In accordance with one embodiment, the tines 30A, 30B are advanced into the bone until the arms 22A, 22B rest flush with the bone surface. Once the tines 30A, 30B are placed as desired, the tool 50 can be removed by moving it proximally along the rod 40A as shown in FIG. 5E. The tool 50 can then be advanced over the other rod 40B and used to urge the proximal tines (such as tine 32A) into the cortical bone to the desired position, as shown in FIG. 5F. Once the tines are positioned in the bone as desired, the two rods 40A, 40B can be urged in opposition directions to bend or otherwise form a curve in the spine 20 as best shown in FIG. 5G. Alternatively, the curve can be formed into the spine 20 before the tines are urged into the bone or after the distal set of tines 30A, 30B are urged into the bone (and before the proximal tines have been so positioned). Both rods 40A, 40B can then be removed as best shown in FIG. 5H such that only the implanted or fixed device 10 remains, as shown in FIG. 5I.

Figure 7:
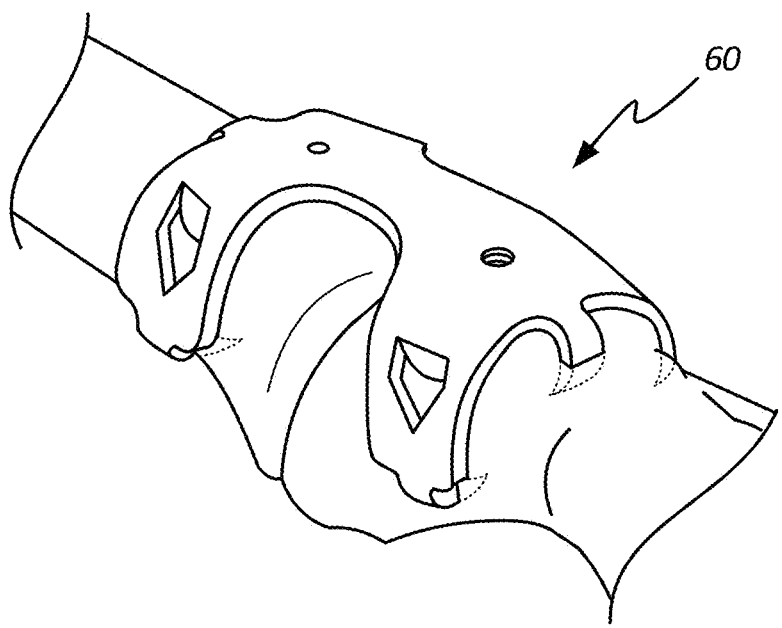
FIG. 7 is a perspective view of a fixation/fusion device implanted or fixed in place across a joint, according to one embodiment.
Figure 8A:
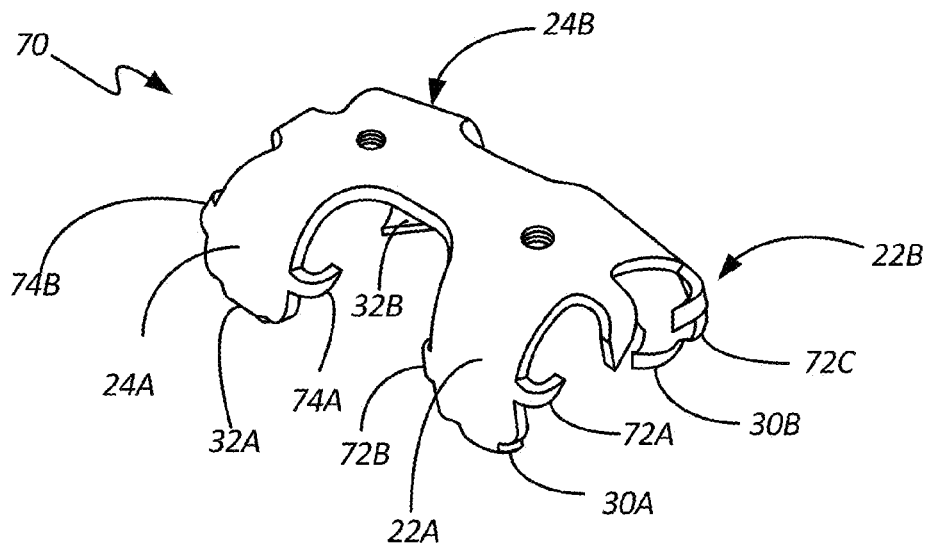
FIG. 8A is a perspective view of a fixation/fusion device, according to another embodiment.
Figure 8B:
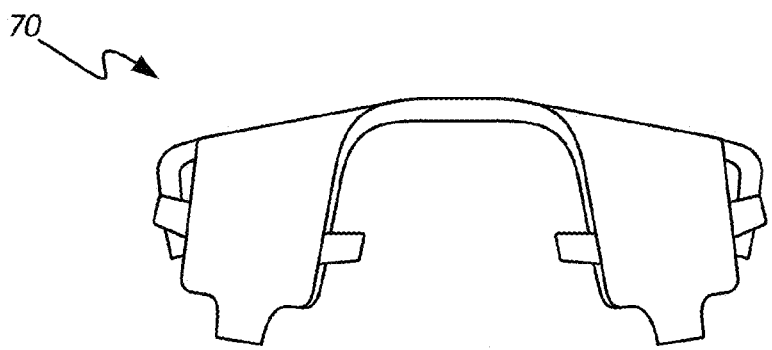
FIG. 8B is a side view of the fixation/fusion device of FIG. 8A.
Figure 8C:
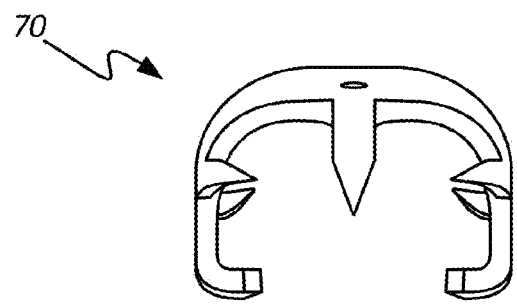
FIG. 8C is an end view of the fixation/fusion device of FIG. 8A.
Figure 8D:
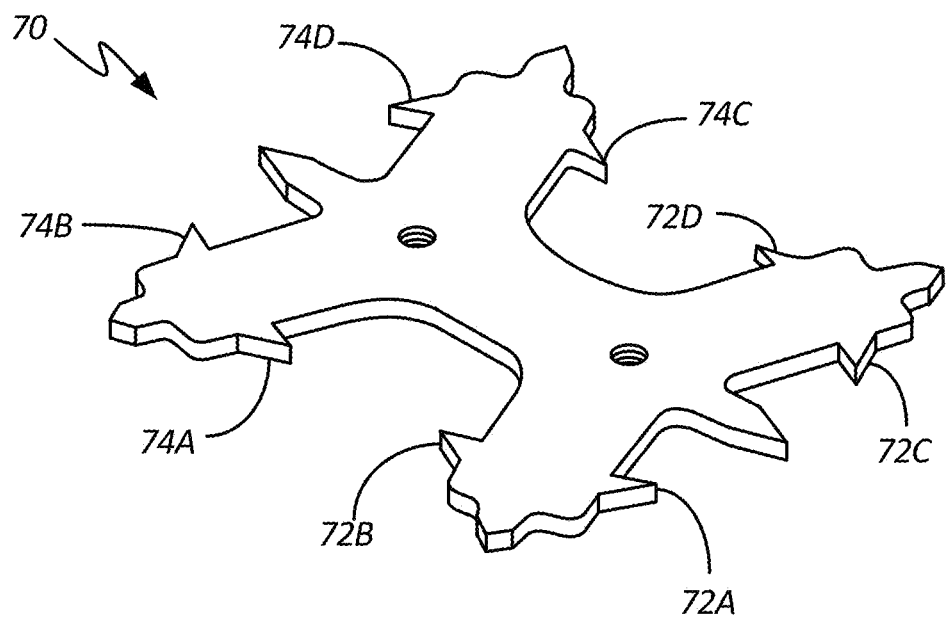
FIG. 8D is a perspective view of the fixation/fusion device of FIG. 8A prior to being formed into the desired shape.

FIGS. 6A-6D and 7 depict another embodiment of a device 60. In this embodiment, each of the arms 22A, 22B, 24A, 24B has two tines—an end tine, and a mid-arm tine that extends from central portion of the arm. Thus, the distal arm 22A has an end tine 30A and a mid-arm tine 62A, while the distal arm 22B has an end tine 30B and a mid-arm tine 62B. Similarly, the proximal arm 24A has an end tine 32A and a mid-arm tine 64A, while the proximal arm 24B has an end tine 32B and a mid-arm tine 64B. FIG. 7 depicts the device 60 implanted at a target site. These additional tines, according to certain implementations, can provide additional rotational stability of the bone with respect to the plate.

Figure 9:
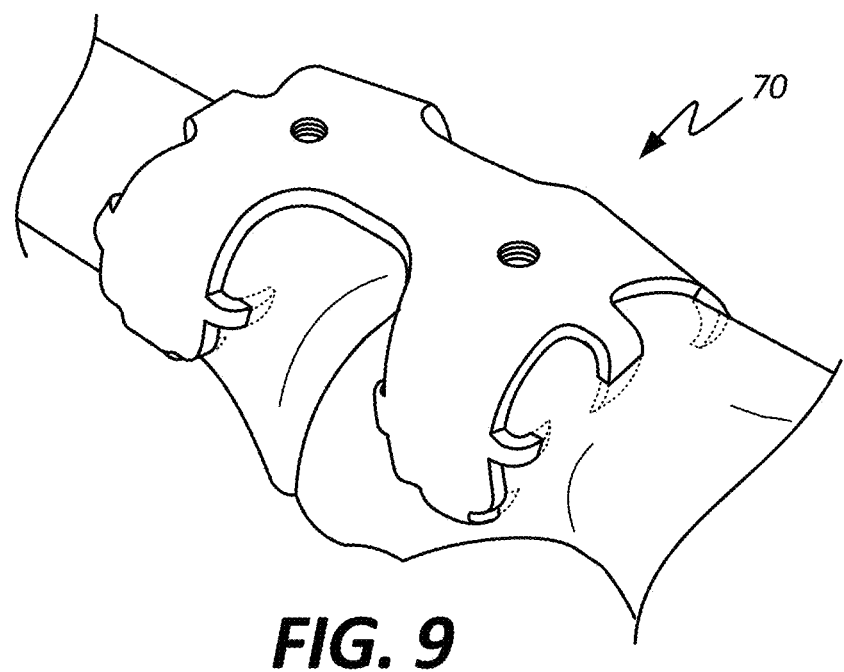
FIG. 9 is a perspective view of a fixation/fusion device implanted or fixed in place across a joint, according to one embodiment.

FIGS. 8A-8D and 9 depict another embodiment of a device 70. In this embodiment, each of the arms 22A, 22B, 24A, 24B has three tines—an end tine, and two mid-arm tines that extend from the sides of the arm. Thus, the distal arm 22A has an end tine 30A and two mid-arm tines 72A, 72B, while the distal arm 22B has an end tine 30B and two mid-arm tines 72C, 72D. Similarly, the proximal arm 24A has an end tine 32A and two mid-arm tines 74A, 74B, while the proximal arm 24B has an end tine 32B and two mid-arm tines 74C, 74D. FIG. 9 depicts the device 70 implanted at a target site. These additional tines can, in some embodiments, provide additional rotational and torsional stability of the bone with respect to the plate.

Figure 10A:
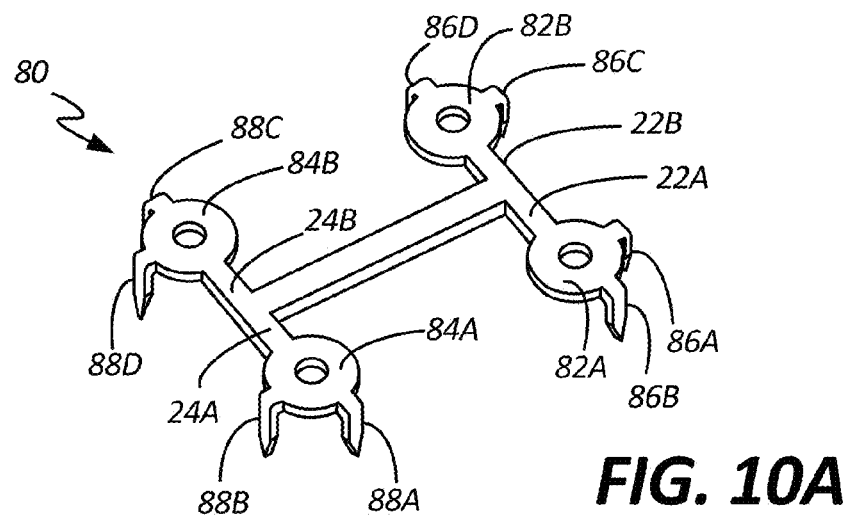
FIG. 10A is a perspective view of a fixation/fusion device, according to another embodiment.
Figure 10B:
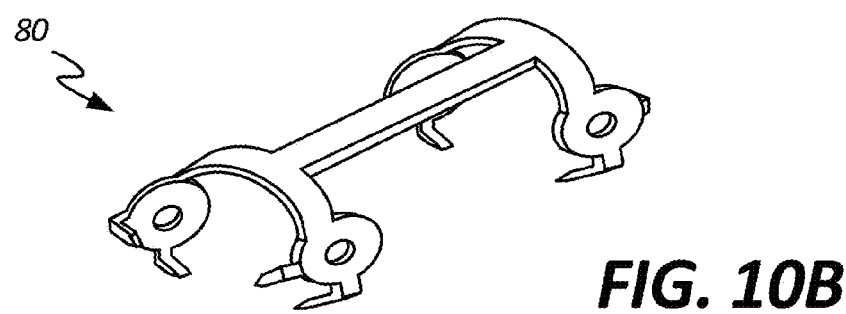
FIG. 10B is a perspective view of the fixation/fusion device of FIG. 10A in which the arms have been deformed into a desired configuration.
Figure 10C:
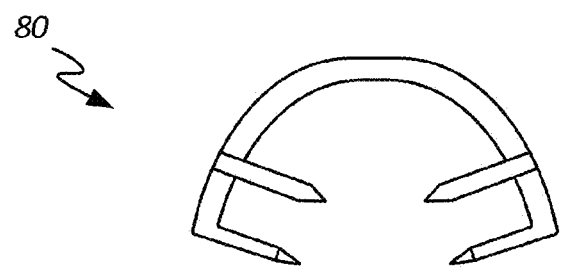
FIG. 10O is an end view of the fixation/fusion device of FIG. 10A.

FIGS. 10A-10C depict another embodiment of a device 80. In this embodiment, each of the arms 22A, 22B, 24A, 24B has a mounting features (in this case, threaded openings) 82A, 82B, 84A, 84B at a distal end of each arm (instead of along the spine), with each of the mounting features 82A, 82B, 84A, 84B having two tines. Thus, the distal arm 22A has a threaded opening 82A having two tines 86A, 86B and the distal arm 22B has a threaded opening 82B having two tines 86C, 86D. Similarly, the proximal arm 24A has a threaded opening 84A having two tines 88A, 88B and the proximal arm 24B has a threaded opening 84B having two tines 88C, 88D. These additional mounting points can provide the surgeon greater control and leverage when working to push the tines into the bone and wrap the arms around the bone.

Figure 11A:
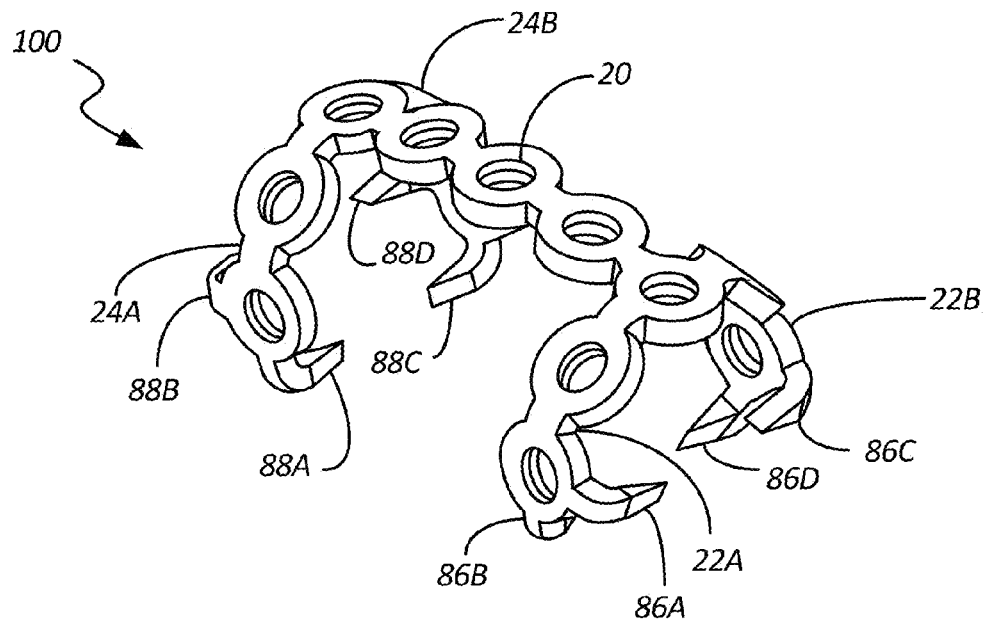
FIG. 11A is a perspective view of a fixation/fusion device, according to another embodiment.
Figure 11B:
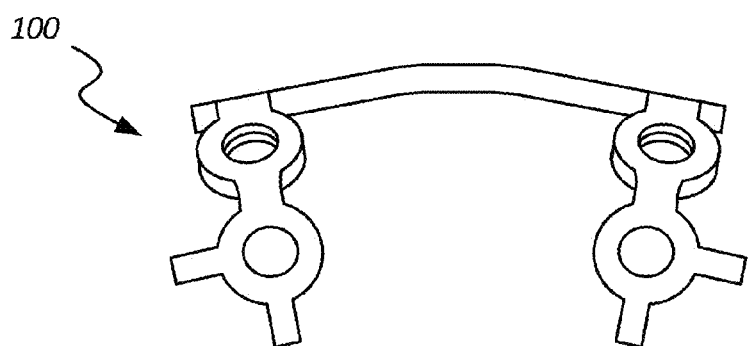
FIG. 11B is a side view of the fixation/fusion device of FIG. 11A.
Figure 11C:
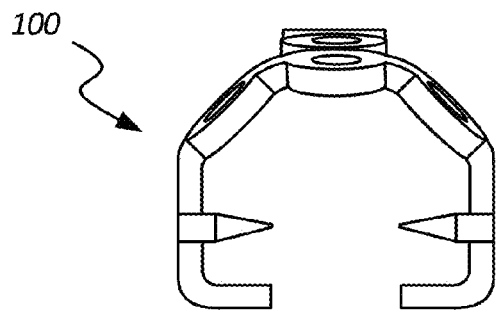
FIG. 11C is an end view of the fixation/fusion device of FIG. 11A.

FIGS. 11A-11C depict another embodiment of a device 100. In this embodiment, the spine 20 has multiple mounting features (threaded openings). In fact, according to certain implementations, the entire spine 20 is made up solely of mounting features that are coupled together. Further, in this implementation, each of the arms 22A, 22B, 24A, 24B is made up of mounting features, with the distal mounting features of each arm having two tines. Thus, the distal arm 22A has two tines 86A, 86B and the distal arm 22B has two tines 86C, 86D. Similarly, the proximal arm 24A has two tines 88A, 88B and the proximal arm 24B has two tines 88C, 88D, in accordance with certain implementations, these mounting features can provide the surgeon flexibility to adjust the device to specific anatomical bends and incorporate additional fixation devices such as screws or locking screws.

Figure 12A:
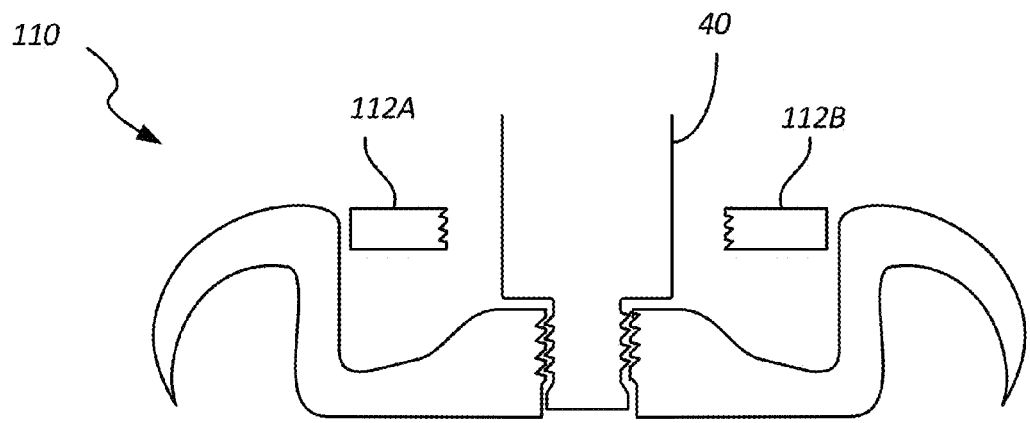
FIG. 12A is a perspective view of a fixation/fusion device coupled to an application tool for purposes of implantation, according to one embodiment.
Figure 12B:
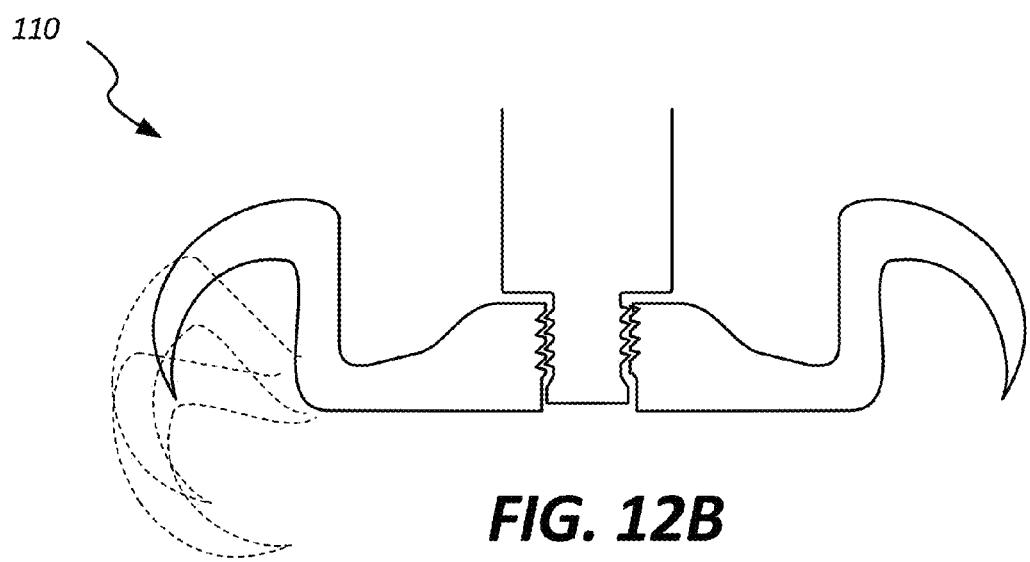
FIG. 12B is a perspective view of the fixation/fusion device of FIG. 12A in which the application tool is urging the tines of the fixation/fusion device into the bone, according to one embodiment.

FIGS. 12A and 12B depict a cross-section cutaway view of a device 110 coupled to an application tool 40, according to one embodiment. In this embodiment, a separate tine advancement tool 112 schematically represented by the small projections 112A, 112B is used to advance the tines into the bone. In this embodiment, the tool 112 applies force away from the rod 40 in a direction that is perpendicular to the longitudinal axis of the rod, thereby urging the tines into the bone as best shown in FIG. 12B.

Figure 13A:
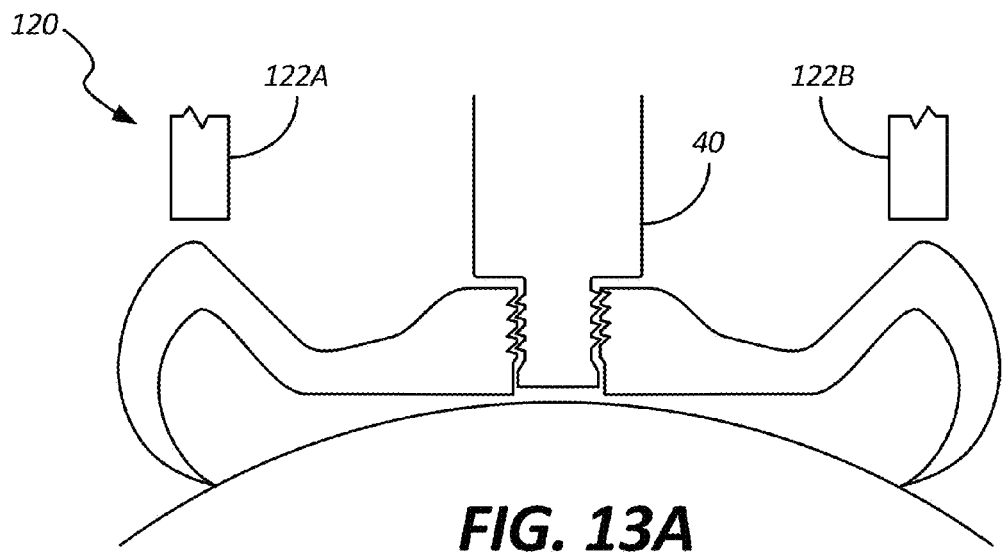
FIG. 13A is a perspective view of a fixation/fusion device coupled to an application tool for purposes of implantation, according to one embodiment.
Figure 13B:
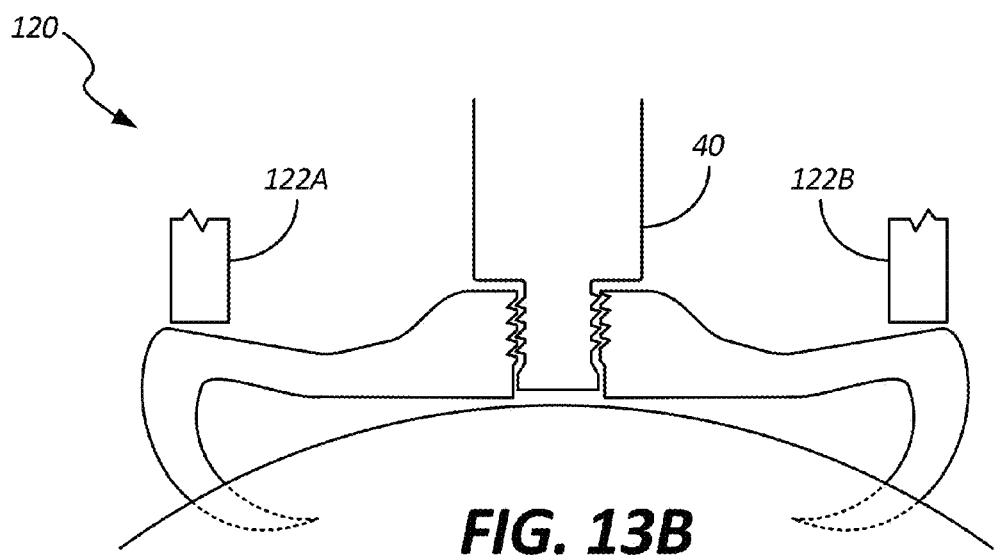
FIG. 13B is a perspective view of the fixation/fusion device of FIG. 13A in which the application tool is urging the tines of the fixation/fusion device into the bone, according to one embodiment.

FIGS. 13A and 13B depict a cross-section cutaway view of a device 120 coupled to an application tool 40, according to one embodiment. In this embodiment, a separate tine advancement tool 122 schematically represented by the small projections 122A, 122B is used to advance the tines into the bone. In this embodiment, the tool 122 applies force toward the bone in a direction that is parallel to the longitudinal axis of the rod 40, thereby urging the tines into the bone as best shown in FIG. 13B.

Figure 14A:
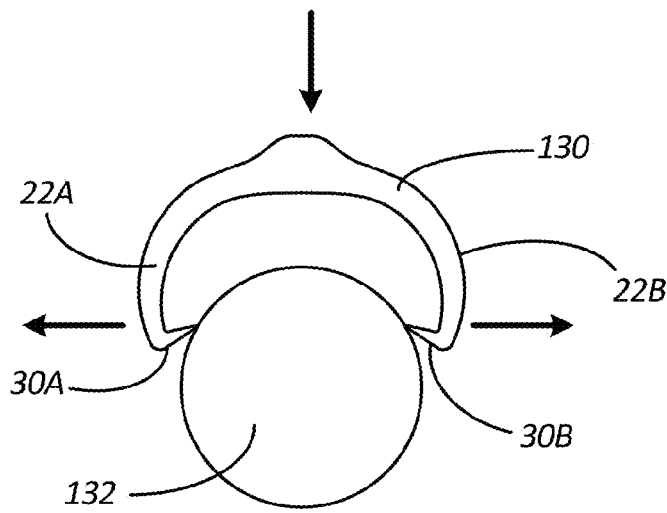
FIG. 14A is a side view of a fixation/fusion device positioned adjacent to a target bone, according to another embodiment.
Figure 14B:
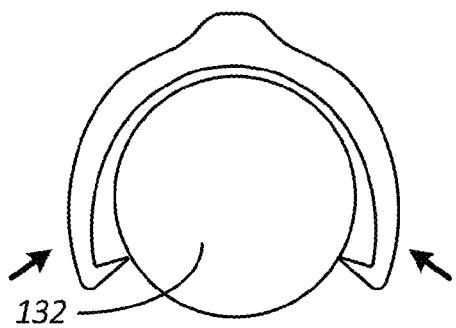
FIG. 14B is a side view of the fixation/fusion device of FIG. 14A in which the device has been positioned around the target bone, according to one embodiment.
Figure 14C:
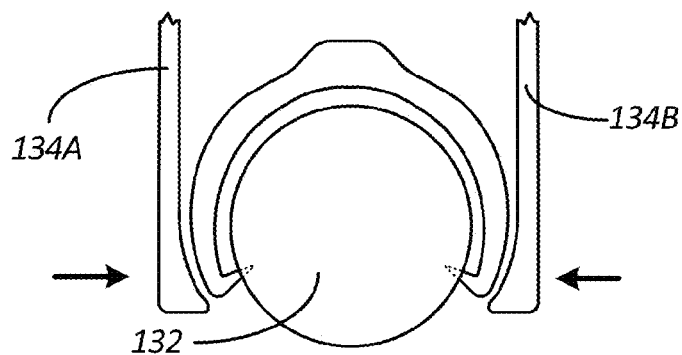
FIG. 14C is a side view of the fixation/fusion device of FIG. 14A in which an application tool is urging the tines of the fixation/fusion device into the bone, according to one embodiment.

FIGS. 14A-14C depict a cross-section cutaway view of a device 130 that is advanced over a target bone 132 and then fixed in place. It is understood that this device 130 can be any of the device embodiments disclosed herein, including, for example, the device 10 described in detail above. In this embodiment, the device 130 is semi-rigid, meaning that it has enough flexibility to allow the arms 22A, 22B to flex outwardly as shown by the arrows in FIG. 14A, thereby allowing the device 130 to be advanced to its desired positioned on the bone 132 as shown in FIG. 14B. A crimping or fixation tool 134 is then positioned such that the arms of the tool 134A, 134B are positioned against the arms 22A, 22B of the device 130. The tool 134 is then actuated to urge the tines 30A, 30B into the bone as shown in FIG. 14C.

Figure 15A:
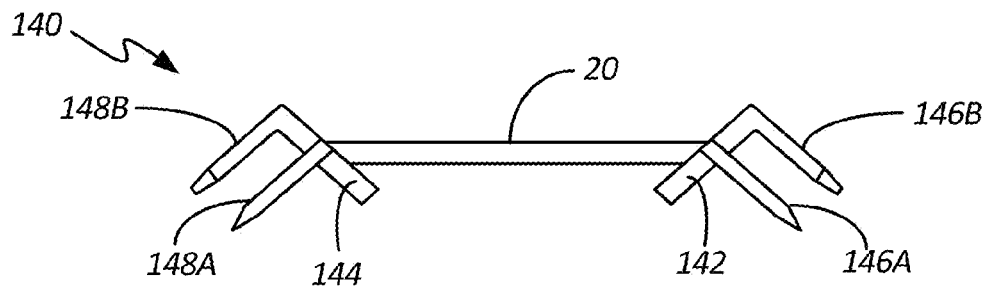
FIG. 15A is a side view of a fixation/fusion device, according to another embodiment.
Figure 15B:
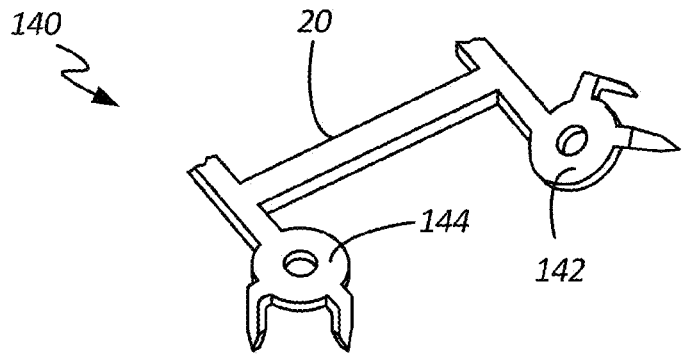
FIG. 15B is a perspective view of the fixation/fusion device of FIG. 15A.
Figure 15C:
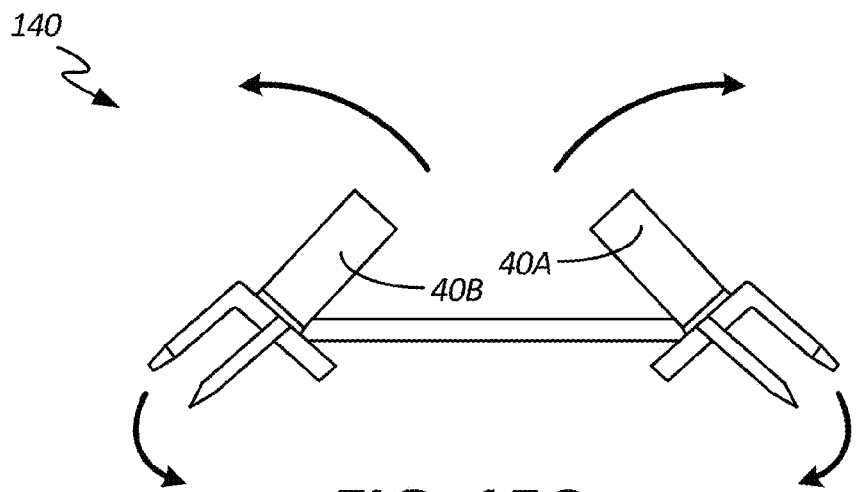
FIG. 15C is a side view of the fixation/fusion device of FIG. 15A coupled to an application tool for purposes of implantation, according to one embodiment.

FIGS. 15A-15C depict another embodiment of a device 140. In this embodiment, the spine 20 has a mounting feature (in this case, threaded openings) 142, 144 at each end, with each of the mounting features 142, 144 having two tines. Thus, the distal end has a threaded opening 142 having two tines 146A, 146B and the proximal end has a threaded opening 144 having two tines 148A, 148B. Further, the two threaded openings 142, 144 are positioned at an angle in relation to the spine 20 as best shown in FIGS. 15A and 15C. Thus, during fixation, the two application rods 40A, 40B can be coupled to the threaded openings 142, 144 and force applied as shown in FIG. 15C to urge the tines into the bone. The resulting rotation of the threaded mounting features 144 and 142 can bring the proximal and distal bone portions towards one another as the tines are advanced.

Figure 16:
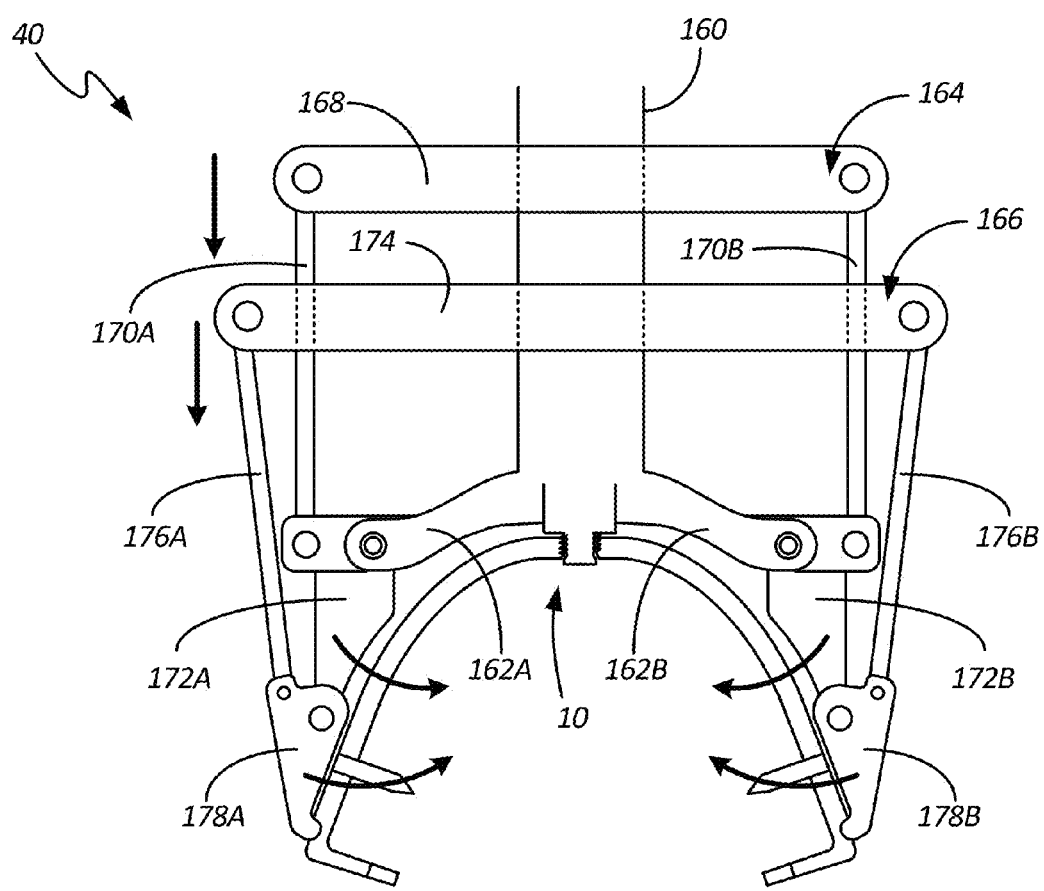
FIG. 16 is a side view of a fixation/fusion device coupled to an application tool for purposes of implantation, according to one embodiment.
Figure 17A:
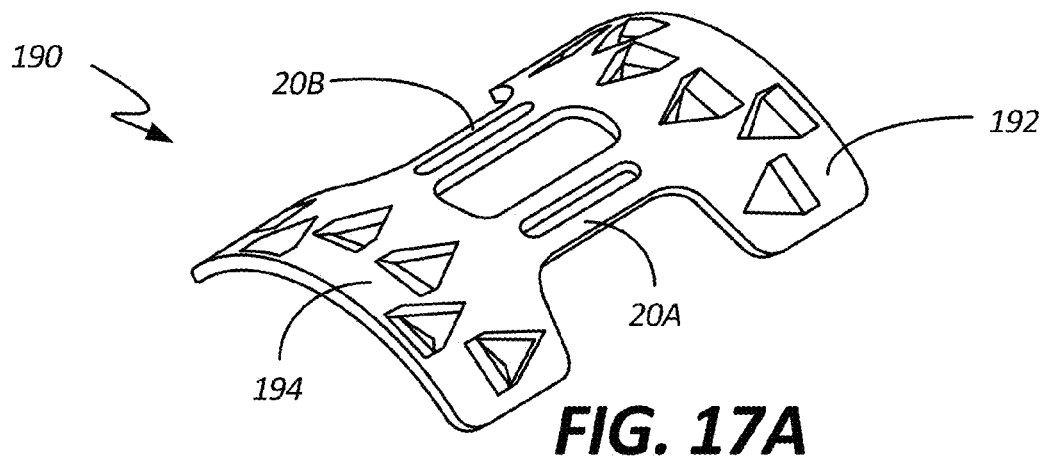
FIG. 17A is a perspective view of a fixation/fusion device, according to another embodiment.
Figure 17B:
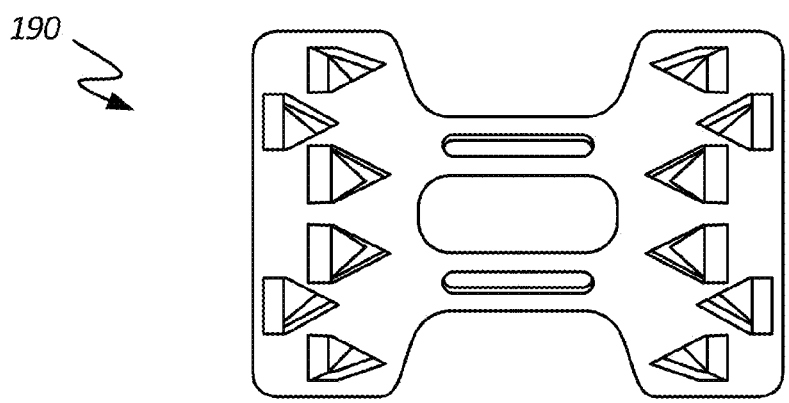
FIG. 17B is a top view of the fixation/fusion device of FIG. 17A.
Figure 17C:
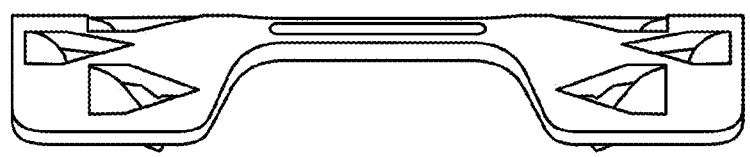
FIG. 17C is a side view of the fixation/fusion device of FIG. 17A.
Figure 17D:
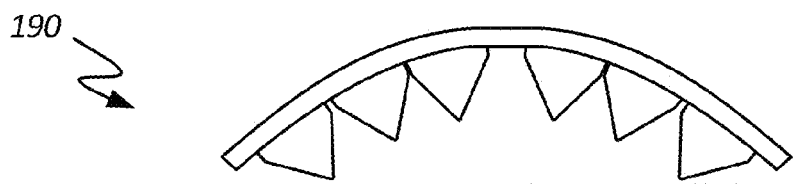
FIG. 17D is an end view of the fixation/fusion device of FIG. 17A.

FIG. 16 shows an application tool 40, according to one embodiment. The tool 40 has a central rod 160 with two arms 162A, 162B at the distal end. The application tool 40 positions or implants the device 10 in two stages: first bending the arms to a certain point, and then applying a further bend that wraps the arms around the bone even further. This is accomplished using two different deployment components 164, 166. The first deployment component 164 has a bar 168 coupled to two links 170A, 170B that are coupled at their distal ends to first pivotal paddles 172A, 172B. The first pivotal paddles 172A, 172B are pivotally coupled to the arms 162A, 162B of the application tool 40, such that when the bar 168 of the first deployment component is urged downward, the distal ends of the first pivotal paddles 172A, 172B contact the arms of the device 10 and bend the arms (urge the arms toward the bone).

Once that is complete, the second deployment component 166 is deployed as follows. The second deployment component 166 has a bar 174 coupled to two links 176A, 176B that are coupled at their distal ends to second pivotal paddles 178A, 178B. The second pivotal paddles 178A, 178B are pivotally coupled to the first pivotal paddles 172A, 172B, such that when the bar 174 of the second deployment component 166 is urged downward, the distal ends of the second pivotal paddles 178A, 178B contact the arms of the device 10 and further bend the arms such that they are more fully wrapped around the bone.

FIGS. 17A-17D depict another embodiment of a device 190. In this embodiment, the device 190 has two spines 20A, 20B with plates coupled to those spines 20A, 20B rather than arms. That is, the device 190 has a distal plate 192 and a proximal plate 194. Each of the plates 192, 194 has multiple tines projecting from the plate as shown. Having a medial and lateral spine offset from the dorsal-most portion of the device lowers the profile of the implant, can provide more lateral support and can provide more clearance for the extensor tendon to sit.

Figure 18:
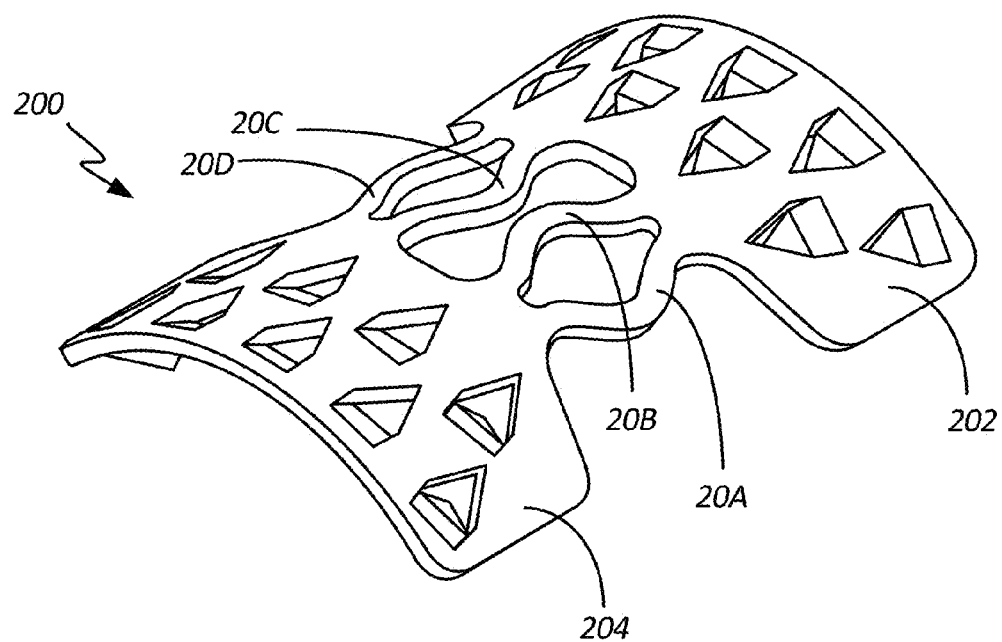
FIG. 18 is a perspective view of a fixation/fusion device, according to another embodiment.

FIG. 18 depicts another embodiment of a device 200. In this embodiment, the device 200 has two split spines (spine 20A, 20B and spine 20C, 20D) with plates coupled to those spines rather than arms. That is, the device 200 has a distal plate 202 and a proximal plate 204. Each of the plates 202, 204 has multiple tines projecting from the plate as shown. This is a depiction of how the surgeon may use an available tool to shorten the effective length of the device post placement by urging the split spines away from each other. Shortening the effective length of the spine brings the proximal and distal portions together, further engaging the tines and bringing the two fusion bones together.

Figure 19A:
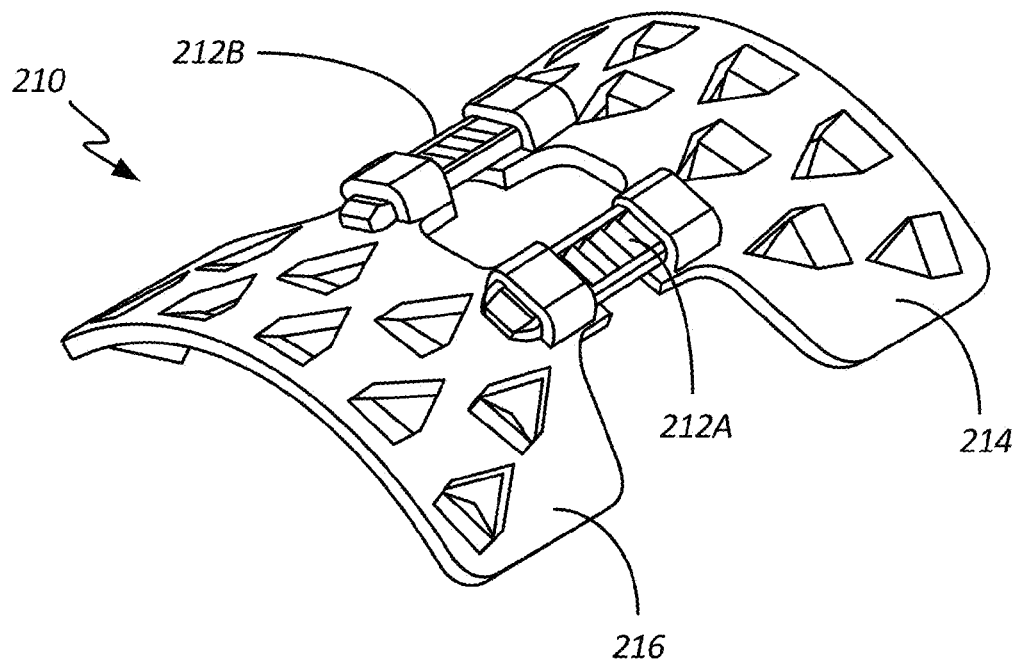
FIG. 19A is a perspective view of a fixation/fusion device with adjustable connection components, according to another embodiment.
Figure 19B:
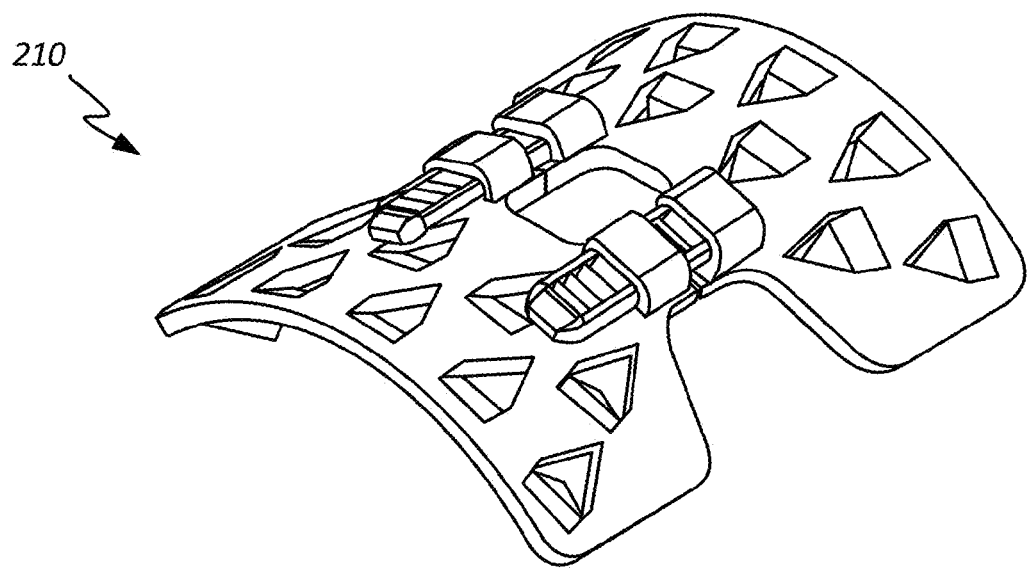
FIG. 19B is a perspective view of the fixation/fusion device of FIG. 19A in which the adjustable connection components have been shortened, according to one embodiment.

FIGS. 19A-19B depict another embodiment of a device 210. In this embodiment, the device 210, instead of a spine or spines, has adjustable connection components 212A, 212B. In one implementation, the adjustable connection components 212A, 212B are zip-tie like components that have adjustable lengths. The components 212A, 212B couple together a distal plate 214 and a proximal plate 216. Each of the plates 214, 216 has multiple tines projecting from the plate as shown. The components 212A, 212B can be shortened to apply force to the bones to which the device 210 is coupled, as shown in FIG. 19B.

Figure 20A:
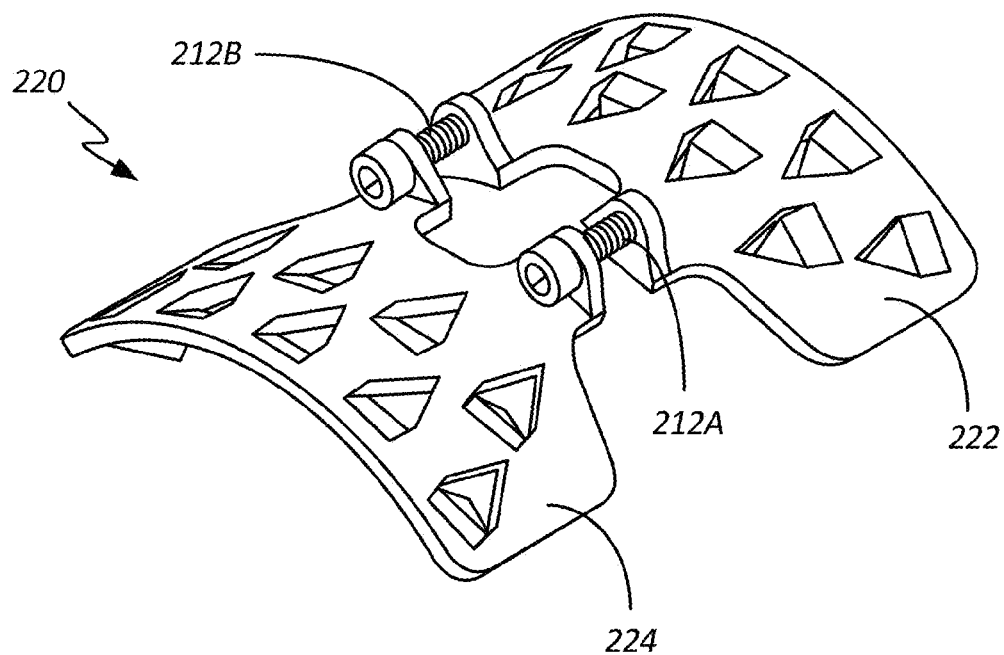
FIG. 20A is a perspective view of a fixation/fusion device with adjustable connection components, according to another embodiment.
Figure 20B:
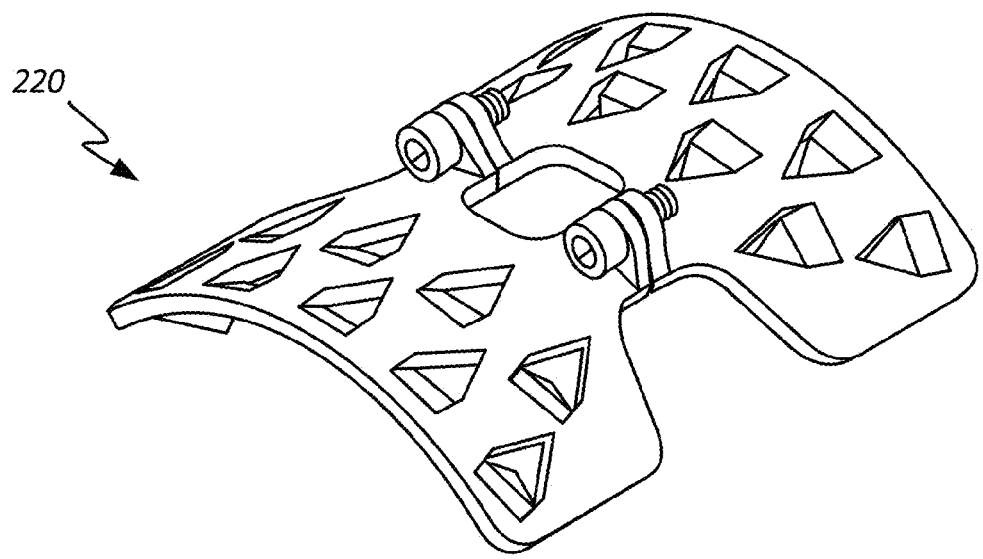
FIG. 20B is a perspective view of the fixation/fusion device of FIG. 20A in which the adjustable connection components have been shortened, according to one embodiment.

FIGS. 20A-20B depict another embodiment of a device 220. In this embodiment, the device 220, instead of a spine or spines, has adjustable connection components 212A, 212B. In one implementation, the adjustable connection components 212A, 212B are adjustable screws. The components 212A, 212B couple together a distal plate 222 and a proximal plate 224. Each of the plates 222, 224 has multiple tines projecting from the plate as shown. The components 212A, 212B can be shortened to apply force to the bones to which the device 220 is coupled, as shown in FIG. 20B.

Figure 21A:
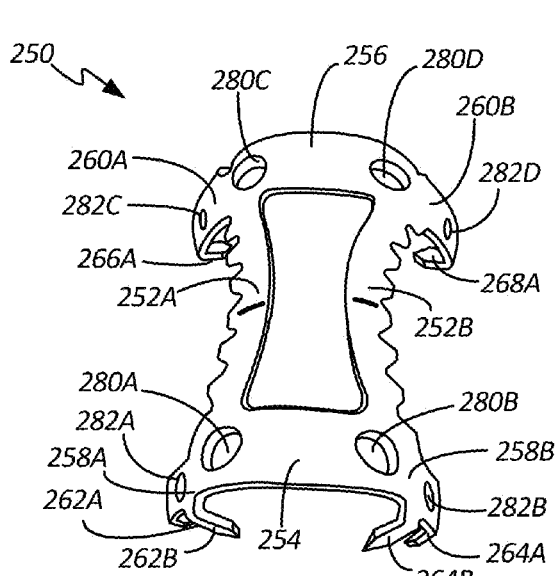
FIG. 21A is a perspective view of a fixation/fusion device, according to another embodiment.
Figure 21B:
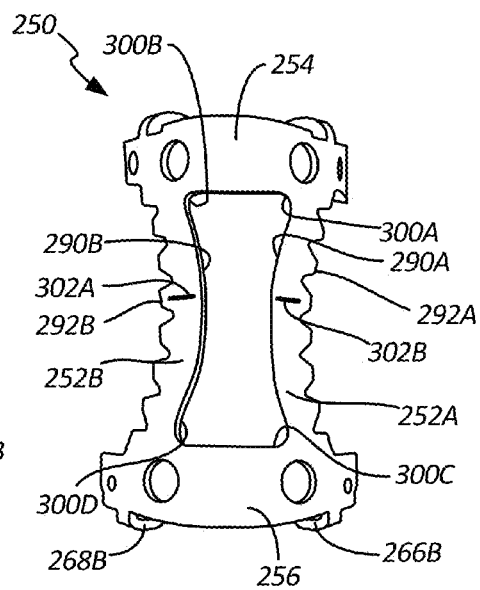
FIG. 21B is a top view of the fixation/fusion device of FIG. 21A.

FIGS. 21A-21E depict another embodiment of a device 250. In this embodiment, the device 250 has two spines 252A, 252B with plates 254, 256 coupled to those spines 252A, 252B. That is, the device 250 has a distal plate 254 and a proximal plate 256. Each of the plates 254, 256 has two arms extending from the plate as shown. More specifically, the distal plate 254 has arms 258A, 258B extending therefrom, while plate 256 has arms 260A, 260B. In this embodiment, each of the arms 258A, 258B, 260A, 260B has two tines—an end tine and a mid-arm tine that extends from the side of the arm. Thus, the distal arm 258A has an end tine 262A and a mid-arm tine 262B, while the distal arm 258B has an end tine 264A and a mid-arm tine 264B. Similarly, the proximal arm 260A has an end tine 266A (as best shown in FIG. 21A) and a mid-arm tine 266B (as best shown in FIG. 21B), while the proximal arm 260B has an end tine 268A (as best shown in FIG. 21A) and a mid-arm tine 268B (as best shown in FIG. 21B).

In this implementation, the device 250 also has four arm deformation features 280A, 280B, 280C, 280D. More specifically, the arm deformation features in this embodiment are four openings 280A, 280B, 280C, 280D configured to facilitate deformation of the arms 258A, 258B, 260A, 260B, as discussed in further detail below. That is, the presence of the openings 280A, 280B, 280C, 280D makes it easier to deform the arms 258A, 258B, 260A, 260B in comparison to an equivalent device without the openings. According to one embodiment, the openings 280A, 280B, 280C, 280D have cross-sectional areas designed to preferentially localize deformation within the device 250 in the area surrounding each opening 280A, 280B, 280C, 280D so that the device 250 more closely approximates the cross section of the target bone when the device 250 is crimped thereto.

According to one embodiment, the device 250 also has four tool interface features 282A, 282B, 282C, 282D. More specifically, the tool interface features in this implementation are four openings 282A, 282B, 282C, 282D configured to couple with a tool, such as a pair of pliers, for purposes of implanting or otherwise positioning the device 250, as discussed in further detail below.

Figure 21C:
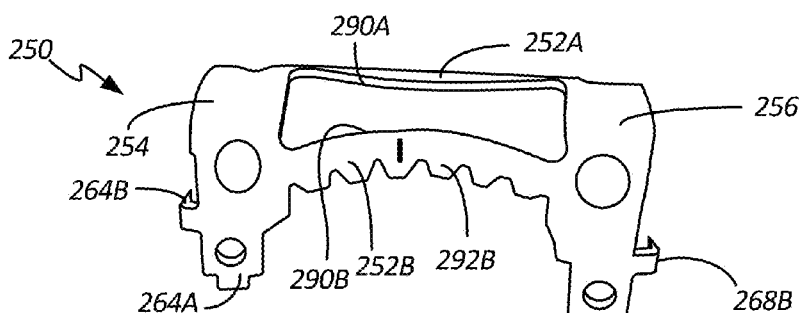
FIG. 21C is a perspective side view of the fixation/fusion device of FIG. 21A.
Figure 21D:
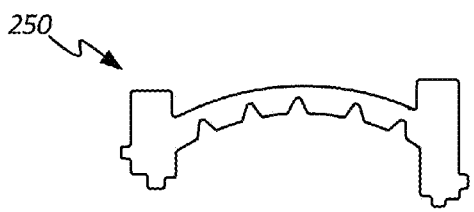
FIG. 21D is a side view of the fixation/fusion device of FIG. 21A.
Figure 21E:
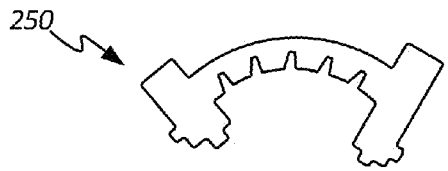
FIG. 21E is a side view of the fixation/fusion device of FIG. 21A.

As best shown in FIGS. 21B and 21C, both of the left 252A and right 252B spines have a curved inner edge 290A, 290B and a notched (or "serrated") outer edge 292A, 292B. This specific configuration of the spines 252A, 252B is designed to facilitate deformation of the spines 252A, 252B, thereby facilitating the creation of an anatomical 3-D shape as the device 250 is implanted in the body of the patient. More specifically, the curved inner edge 290A, 290B and notched outer edge 292A, 292B allow for the spines 252A, 252B to be deformed or "bent" such that the plates 254, 256 are urged downward in relation to the middle of the spines 252A, 252B more easily than if the spines 252A, 252B did not have the curved inner edges 290A, 290B and the notched outer edges 292A, 292B. As one specific example, FIGS. 21D and 21E depict this feature of the device 250. More specifically, FIG. 21D depicts the device 250 in its undeformed state, while FIG. 21E depicts the device 250 in its deformed state as described above.

As best shown in FIG. 21B, each of the spines 252A, 252B also have spine corners 300A, 300B, 300C, 300D where each of the spines 252A, 252B are coupled to the plates 254, 256. These spine corners 300A, 300B, 300C, 300D facilitate stability and are radiused to prevent fatigue fracture.

As also best depicted in FIG. 21B, each of the spines 252A, 252B also has a joint or fracture site indicator line 302A, 302B that can be used to align the device 250 with the target joint or fracture, as will be described in further detail below.

Figure 22:
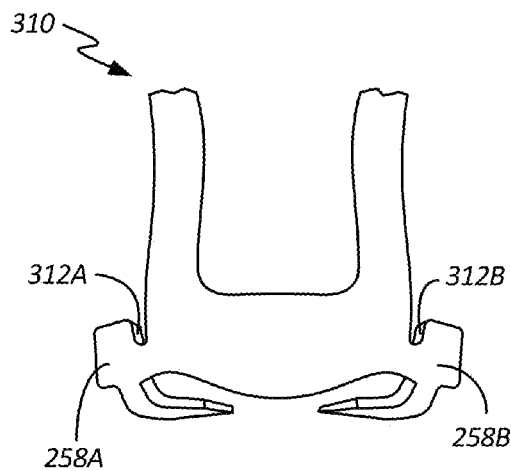
FIG. 22 is a top view of a fixation/fusion device, according to another embodiment.
Figure 23:
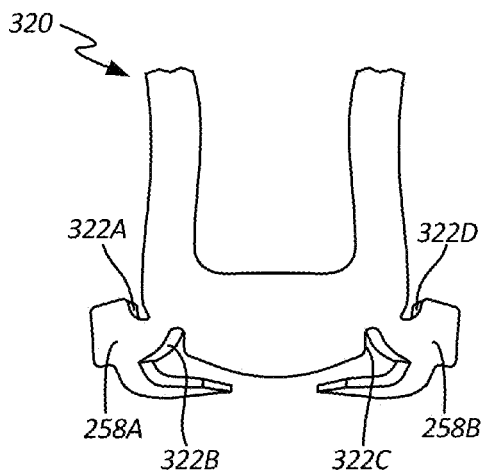
FIG. 23 is a top view of a fixation/fusion device, according to another embodiment.

FIGS. 22 and 23 depict two alternative embodiments of devices 310, 320. For example, the device 310 has arm deformation features 312A, 312B that are notches 312A, 312B defined in the arms 258A, 258B. Further, the device 320 has arm deformation features 322A, 322B, 322C, 322D that are notches 322A, 322B, 322C, 322D defined in the arms 258A, 258B. These arm deformation features as shown in these alternative embodiments can be similar in function to the arm deformation features 280A, 280B, 280C, 280D discussed above with respect to the device 250. More specifically, these arm deformation features 312A, 312B and 322A, 322B, 322C, 322D reduce the cross-section of the arms, thereby facilitating deformation thereof.

Figure 24A:
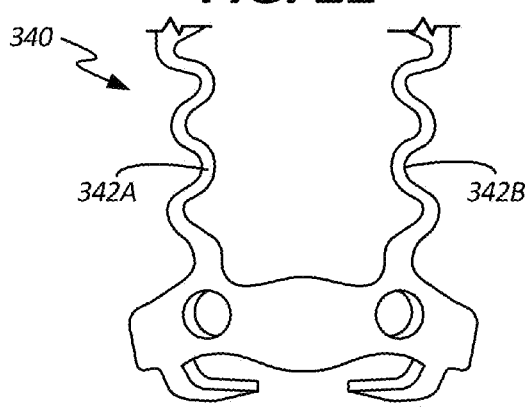
FIG. 24A is a top view of a fixation/fusion device, according to another embodiment.
Figure 24B:
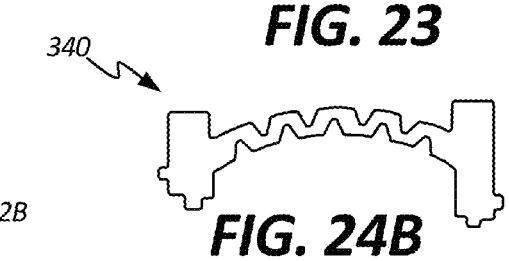
FIG. 24B is a side view of the fixation/fusion device of FIG. 24A.
Figure 24C:
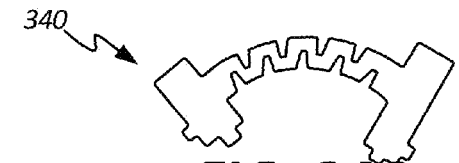
FIG. 24C is a side view of the fixation/fusion device of FIG. 24A.

FIGS. 24A-24C depict a further implementation of a device 340. In this embodiment, the device 340 has two spines 342A, 342B, both of which are curvy (or "zig-zagged") spines 342A, 342B that facilitate spine deformation. That is, much like the curved inner edges 290A, 290B and notched outer edges 292A, 292B described above, the curvy spines 342A, 342B allow for the spines 342A, 342B to be deformed or "bent" more easily than if the spines 342A, 342B did not have a curvy configuration. As one specific example, FIGS. 24B and 24C depict this feature of the device 340. More specifically, FIG. 24B depicts the device 340 in its un-deformed state, while FIG. 24C depicts the device 340 in its deformed state as described above.

Figure 25:
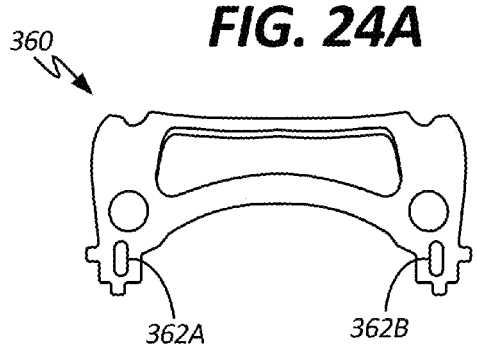
FIG. 25 is a side view of a fixation/fusion device, according to another embodiment.
Figure 26:
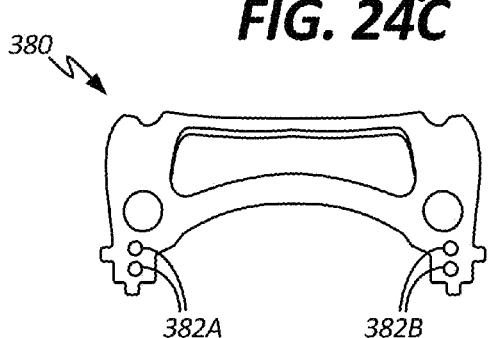
FIG. 26 is a side view of a fixation/fusion device, according to another embodiment.

FIGS. 25 and 26 depict two additional alternative embodiments of devices 360, 380. For example, the device 360 has four tool interface features 362A, 362B (other two features not visible as depicted) that are oval openings 362A, 362B configured to couple with a tool, such as a pair of pliers, for purposes of implanting or otherwise positioning the device 360, as discussed in further detail below. Similarly, the device 380 has four tool interface features 382A, 382B (the other two features not visible as depicted) that are each made up of two openings 382A, 382B configured to couple with a tool, such as a pair of pliers. In both of these alternative embodiments, the features 362A, 362B, 382A, 382B are non-circular or multiple openings to prevent rotation when the tool is coupled thereto.

Figure 27:
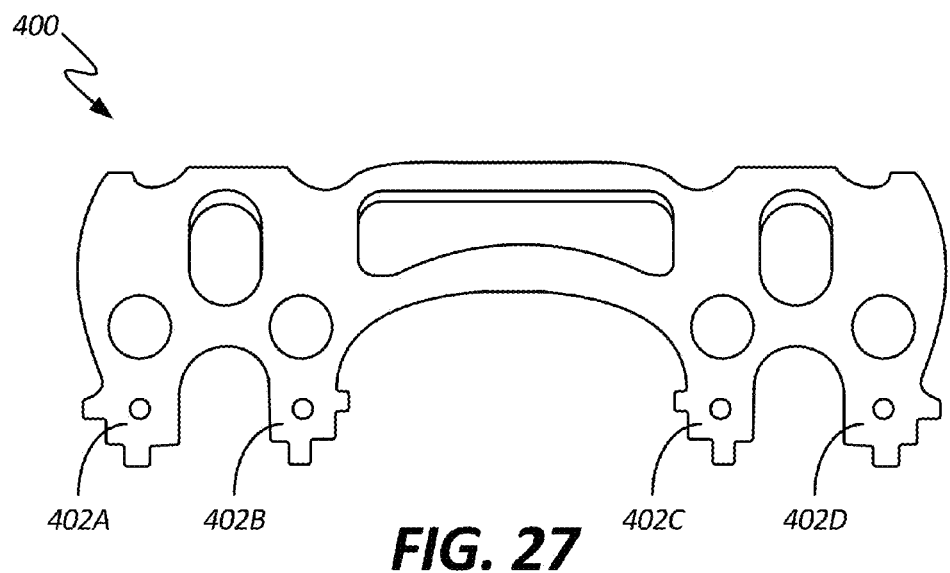
FIG. 27 is a side view of a fixation/fusion device, according to another embodiment.

FIG. 27 depicts a further alternative embodiment of device 400, which has eight arms 402A, 402B, 402C, 402D (with the other four arms not visible as depicted) instead of four. Such an implementation increases stability and robustness, which can be useful in applications that have higher loads (such as joint fixation of the big toe, for example) or for bone fracture fixation.

Figure 28:
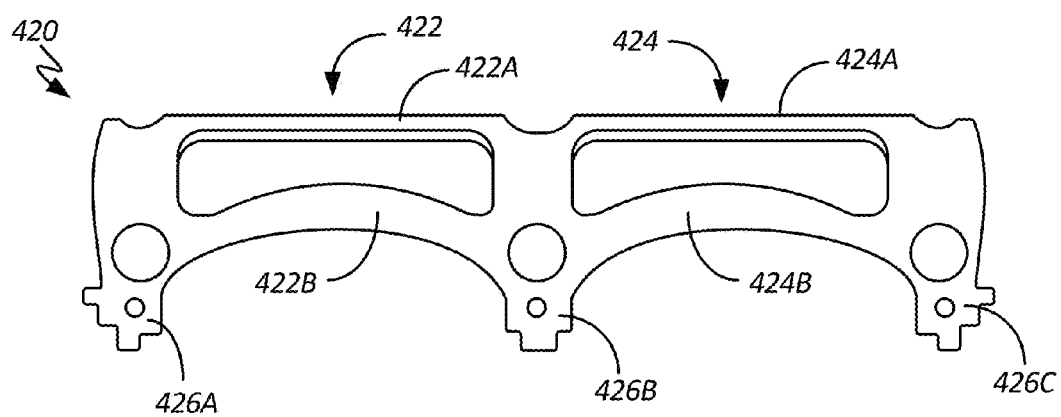
FIG. 28 is a side view of a fixation/fusion device, according to another embodiment.

FIG. 28 depicts yet another alternative embodiment of a device 420 having two spine sections 422, 424, with each of the sections having two spines 422A, 422B, 424A, 424B, along with six arms 426A, 426B, 426C (with the other three arms not visible as depicted) instead of four. Such an implementation maintains stability over longer fixation distances, which can be useful in applications such as bone fracture fixation where more than two anchor points are desired.

Figure 30A:
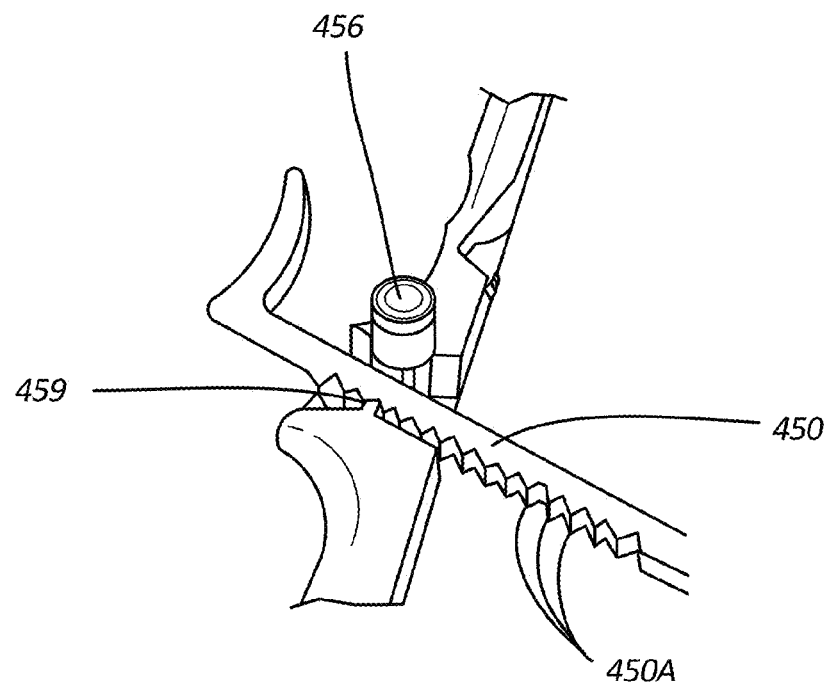
FIG. 30A is an expanded perspective view of the locking mechanism of the implantation device of FIG. 29A.
Figure 30B:
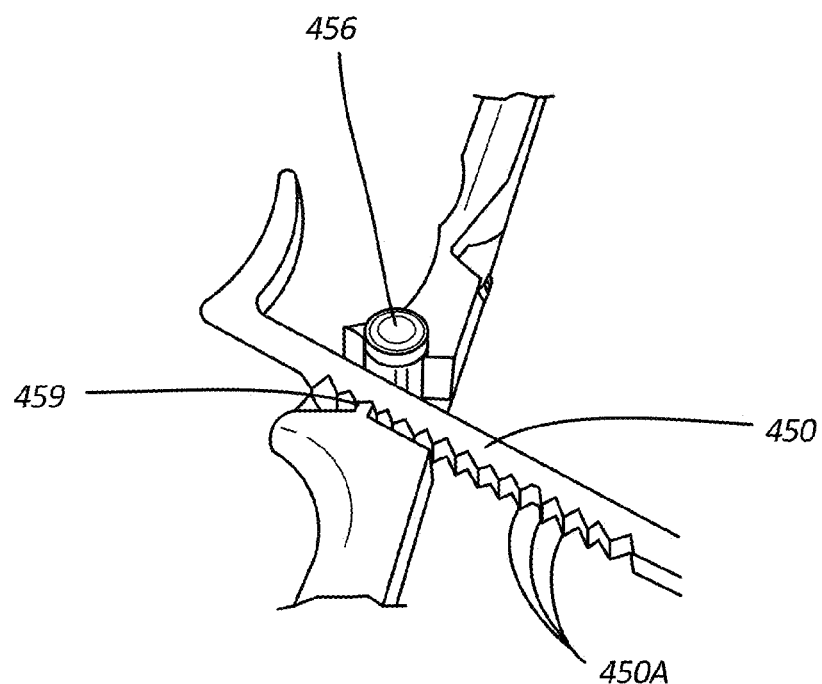
FIG. 30B is an expanded perspective view of the locking mechanism of the implantation device of FIG. 29A.

FIGS. 29A-29C depict a placement or implantation tool 440, which in this specific exemplary embodiment is a pair of pliers 440. The pair of pliers 440 has a pair of jaws 442A, 442B, a jaw pivot 444, and a pair of handles 446A, 446B. Further, as best shown in FIG. 29C, the pair 440 also has a ratchet mechanism 448 that includes a ratchet bar 450, a ratchet spring 452, a ratchet pivot 454, a locking mechanism 456, and a release mechanism 458. The spring 452 is configured to be tensioned to urge the ratchet bar 450 toward the spring 452, thereby urging the teeth 450A on the bar toward the finger 459 (as best shown in FIGS. 30A and 30B) such that the finger 459 is positioned between two of the teeth 450A and retained in that position such that the ratchet bar 450 is retained in that position. The release mechanism 458 in this specific embodiment is a release trigger 458 that can be depressed by a user to urge the bar 450 away from the finger 459 and thereby allow the bar 450 to be moveable in relation to the finger 459, thereby allowing the handles 446A, 446B to move in relation to each other.

As best shown in FIG. 29B, each of the jaws 442A, 442B has a device coupling feature 460A, 460B on an interior surface at the distal end of the jaw 442A, 442B. Each of the features 460A, 460B is configured to interface with and couple with any of the device embodiments disclosed or contemplated here. More specifically, in certain implementations, the coupling features 460A, 460B are configured to couple with tool interface features on the device (such as, for example, the tool interface features 282A, 282B, 282C, 282D described above). In this specific exemplary implementation, the first coupling feature 460A is a circular pin 460A and the second coupling feature 460B is a square peg 460B. These features 460A, 460B and the corresponding tool interface features (such as features 282A, 282B, 282C, 282D described above) are configured to couple together to keep the device (such as device 250, for example) locked in all degrees of freedom when it is coupled to the pair of pliers 440. In an alternative embodiment, the two features 460A, 460B can be a single feature that is non-circular, a multiple pin feature, or any other known feature for achieving the same effect.

FIGS. 30A and 30B depict one embodiment of the locking mechanism 456. More specifically, in this embodiment, the locking mechanism 456 is a locking button 456 that can be depressed by a user to move the locking button 456 into and out of a locked position. FIG. 30A depicts the locking button 456 in the unlocked position, while FIG. 30B depicts the locking button 456 in the locked position in which the button 456 is positioned to urge the ratchet bar 450 toward the finger 459 such that the finger 459 is positioned between two teeth 450A, thereby engaging the bar 450 such that the handles 446A, 446B are restrained from moving in relation to each other. The locking mechanism 456 can be depressed by the user to lock the handles 446A, 446B into a specific orientation. When the locking mechanism 456 is employed to urge the ratchet bar 450 toward the finger 459, the entire device 440 is rigidly fixed and cannot be released by actuating the release mechanism 458. If the lock 456 is unlocked (in the unlocked position) and the release mechanism 458 is engaged (not actuated to release the ratchet bar 450), then the handles 446A, 446B may be compressed (urged toward each other) but cannot be urged away from each other to cause the jaws 442A, 442B to separate from each other. If the lock 456 is unlocked and the release mechanism 458 is actuated, then the handles 446A, 446B may be compressed or released with respect to each other.

It is understood that any of the device embodiments disclosed or contemplated herein can be bent or otherwise deformed along the spine (or spines) into a curved configuration. Such exemplary curved configurations are shown in FIG. 3B and FIG. 32F (discussed below). This spine deformation can occur at anytime (from the manufacturing process forward).

Figure 32A:
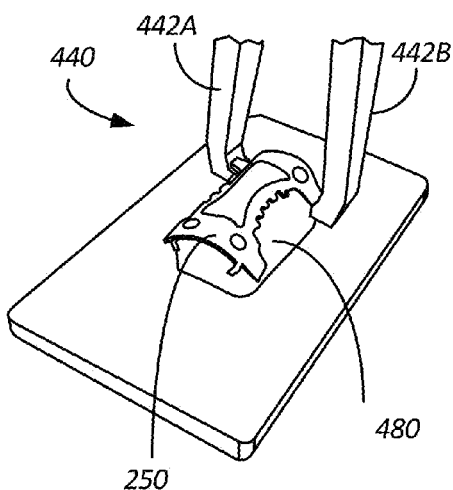
FIG. 32A is a perspective view of a fixation/fusion device on a holder block and coupled to an application tool, according to one embodiment.
Figure 32B:
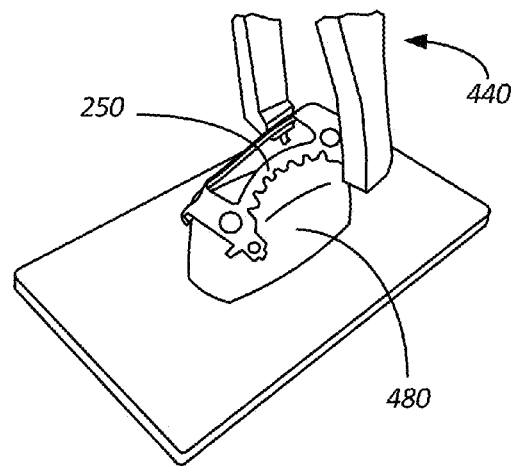
FIG. 32B is a perspective view of the application tool removing the fixation/fusion device of FIG. 32A from the holder block, according to one embodiment.

In use in accordance with one embodiment, the device 250 (and any of the other device embodiments disclosed or contemplated herein) can be placed onto, implanted, or fixed on the desired target site according to the following steps. As shown in FIG. 32A, the first step in certain implementations is to remove the device 250 positioned on the holder block 480 from the device packaging and couple the pliers 440 to it. To do that, the user can urge the locking button 456 on the pliers 440 into the unlocked position as shown in FIG. 30A, thereby making it possible to move the handles 446A, 446B in relation to each other, thereby allowing the jaws 442A, 442B to be moved into a desired configuration to position them around the device 250. Then the pair of pliers 440 can be positioned such that the device coupling features 460A, 460B are coupled with the appropriate tool interface features as shown in FIG. 32A. At this point, the user can lock the pliers jaws 442A, 442B using the locking button 456 as described above, thereby locking the jaws 442A, 442B in position coupled to the device 250. As shown in FIG. 32B, the user can then use the pliers 440 to urge the device 250 away from the holder block 480.

Figure 32C:
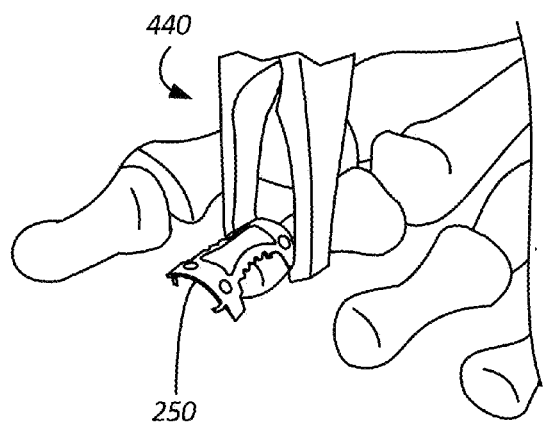
FIG. 32C is a perspective view of the application tool positioning the fixation/fusion device of FIG. 32A at a target bone site, according to one embodiment.
Figure 32D:
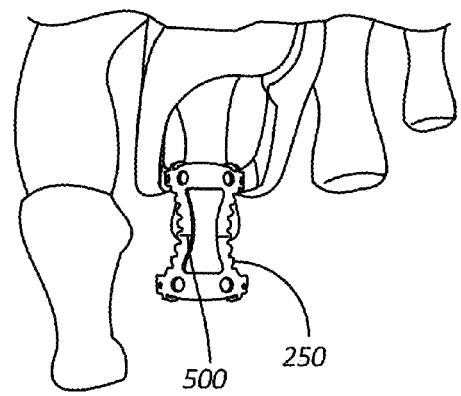
FIG. 32D is a perspective view of the application tool crimping the fixation/fusion device of FIG. 32A in place at the target bone site, according to one embodiment.

Next, as depicted in FIG. 32C, the device 250 can then be positioned over the appropriate portion of the target site using the pliers 440 such that the tines are positioned against or adjacent to the correct portion of the bone. Further, as shown in FIG. 32D, the device 250 has a joint or fracture site indicator line 500 that the user can align with the target joint or fracture using the pliers 440, thereby ensuring that the device 250 is positioned correctly. The user can then urge the locking button 456 into the unlocked position and then crimp the device 250 at the first end using the pliers 440 until the tines of the device 250 are fully advanced into the bone. In one embodiment, the pre-crimped shape of the device 250 and the placement of the tool interface features on the device 250 facilitate the deformation of the device 250 such that it closely conforms to the anatomical cross-section of the target bone, thereby minimizing the gap between the device 250 and the bone after crimping and thus limiting potential tissue irritation.

Once the arms at one end of the device 250 have been fully crimped onto the bone, the pliers 440 are removed from the device 250 by sufficiently spreading the jaws 442A, 442B such that the features 460A, 460B disengage from the device 250. Then, as shown in FIG. 32E, the user then couples the jaws 442A, 442B to the other end of the device 250 by operating the pliers 440 as described previously above, positions the device 250 over the second section of the target bone, ensuring close approximation to the joint or fracture, and crimps the device 250 at that end until the tines of the device 250 are fully advanced into the bone.

The user can then release the pliers 440 and remove them from the device 250, resulting in a fully implanted device as shown in FIG. 32F. According to one embodiment as shown in which the device 250 is being used to correct hammertoe, the desired result is a 10 to 20 degree bend across the bone joint to replicate the anatomic positioning of the toe. If necessary, this bend can be accomplished by the user manually manipulating the device 250 as described elsewhere herein.

It is also understood that the device 250 (or any device as disclosed or contemplated herein) can also be removed as shown in FIG. 33. More specifically, any known removal tool 520 (such as a mini-hohmann elevator or similar tool) can be used, with the end of the tool 520 being inserted into any one of the four deformation openings 280A, 280B, 280C, 280D and utilize leverage to pry the device 250 from the bone as shown until all the tines are extracted from the bone and provide sufficient clearance to remove the device 250.

Figure 34A:
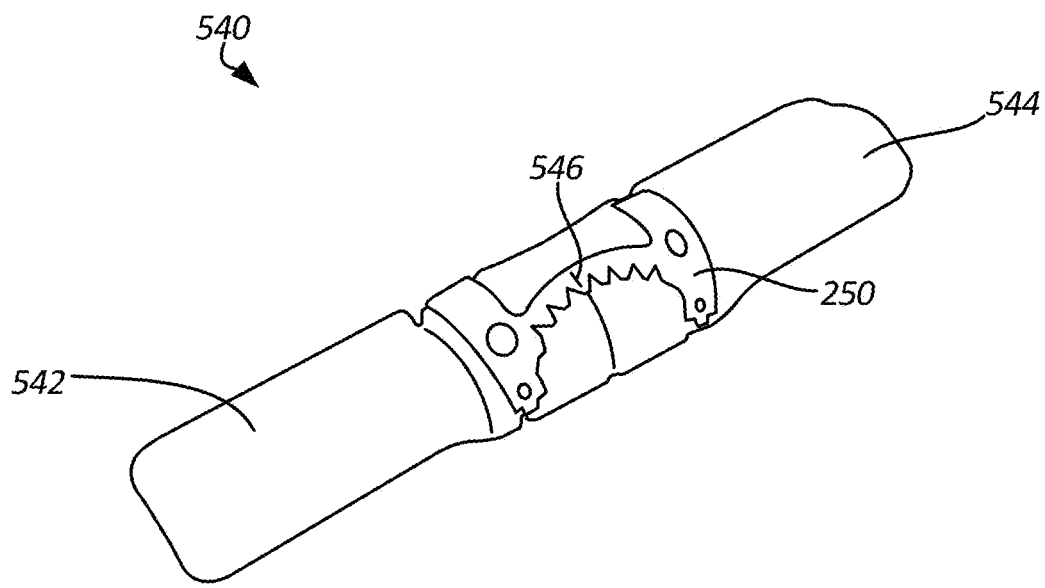
FIG. 34A is a perspective view of a fixation/fusion device on another holder block, according to another embodiment.
Figure 34B:
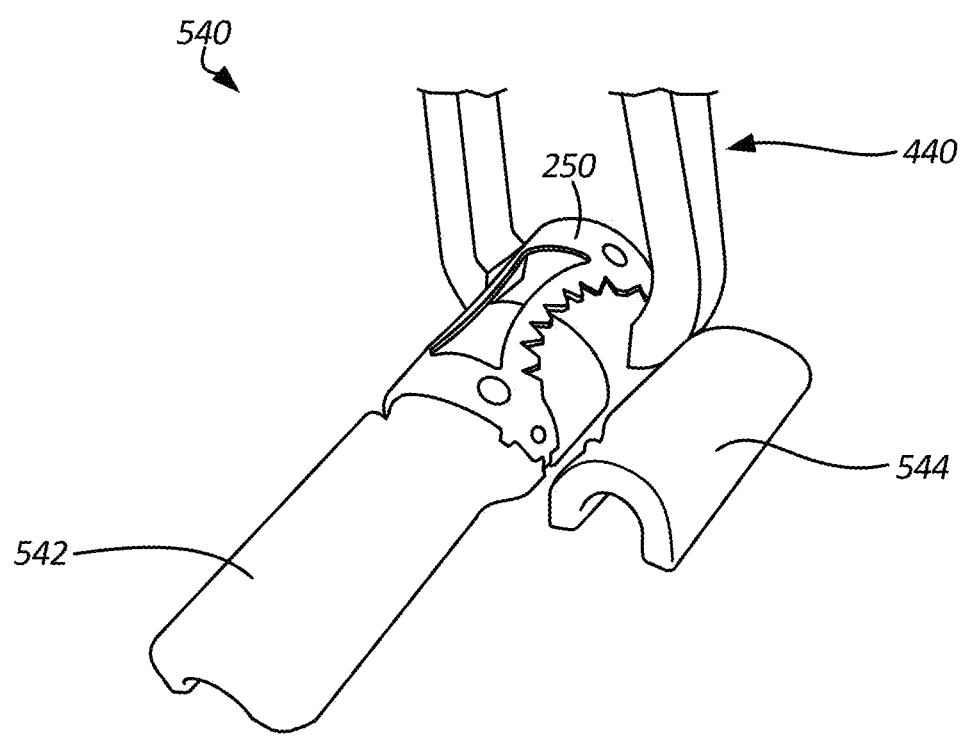
FIG. 34B is a perspective view of the fixation/fusion device of FIG. 34A being removed from the holder block using an implantation tool, according to one embodiment.

An alternative embodiment of a holding block 540 is depicted in FIGS. 34A and 34B. This block 540 is a split holding block 540 comprised of a distal block 542 and a proximal block 544. In this embodiment, the split between the two blocks 542, 544 can represent the joint or fracture of the target bone such that the device 250 is positioned with the indication line 546 aligned with the split. In accordance with one implementation, the block 540 is curved to mate with the device 250 geometry.

In use, as shown in FIG. 34B, a user can use a pliers 440 to couple to the device 250 as described above such that one end of the device 250 can be removed from the block 540. According to one embodiment, the advantage of the split holding block 540 is that the device 250 can be coupled to the first bone portion without having to remove the second portion of the split holding block 540 (in this case, the second portion being the distal portion 542 as shown), thereby providing a stable base (in the form of the distal block 542) for attaching the pliers 440 to the second end of the device 250.

Some of the advantages of certain embodiments disclosed herein include the following. The tine length can be short enough that when fully engaged into the bone there is sufficient room within the central portion of the bone to accommodate a "K-wire." Further, certain embodiments provide the benefits of an extra-medullar placement without the drawbacks of using mounting hardware such as screws. Some devices disclosed herein can be positioned and affixed so that they are stable using one of the application tools disclosed or contemplated herein. In addition, certain implementations herein are configured to be utilized as the sole means of fusion/fixation and can be utilized in conjunction with an additional provisional or planned adjunctive intramedullary "K-wire" per the clinical need and/or surgeon preference.

In some implementations, the specific position, dimension and relationship of the tines provide anatomic specific mechanical stability to the intended digital arthrodesis. Furthermore, the anatomic position of the intended arthrodesis site can modulate to a patient specific position, ensuring a physiologic "slightly flexed" digital arthrodesis. This design feature is an improvement over many intra-medullary digital fixation devices as these devices do not readily allow a physiologic "slightly flexed" digital arthrodesis position when additional "k-wire" fixation of the anatomy is also required.

As discussed above, the various embodiments herein may be used in conjunction with a "K-Wire" or other intramedullar device. The intramedullar device may be placed prior to the application of the device embodiment to aide in the alignment and approximation of the metatarsophalangeal joint. After the device embodiment has been engaged into the metatarsophalangeal joint, the intramedullar device may be removed immediately, removed after a prescribed healing period or left in permanently depending on the type used.

The various embodiments may also be used in conjunction with known fasteners. In certain embodiments, the device can incorporate specialized holes for the use of fasteners when addition support or fixation is required in specific areas. Additionally the device embodiments can be used in conjunction with a screw placed in the central axis of the bone.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Although the present invention has been described with reference to preferred embodiments, persons skilled in the art will recognize that changes may be made in form and detail without departing from the spirit and scope of the invention.

What is claimed is:

1. A bone fixation device comprising:
   (a) at least one spine;
   (b) at least two distal arms extending from a distal end of the at least one spine, each of the at least two distal arms comprising at least one distal bone tine, wherein the at least two distal arms are configured to be positionable around a bone;
   (c) at least two proximal arms extending from a proximal end of the at least one spine, each of the at least two proximal arms comprising at least one proximal bone tine, wherein the at least two proximal arms are configured to be positionable around a bone; and
   (d) at least one opening defined in the bone fixation device, wherein the opening is sized and shaped to receive a portion of an implantation tool.

2. The bone fixation device of claim 1, wherein the at least one spine comprises a first spine and a second spine.

3. The bone fixation device of claim 2, wherein the first and second spines comprise notches defined along a length of each of the first and second spines.

4. The bone fixation device of claim 2, wherein the first and second spines are curvy spines.

5. The bone fixation device of claim 1, wherein the opening comprises internal threads, wherein the internal threads are configured to receive external threads of the implantation tool.

6. The bone fixation device of claim 1, wherein the at least one opening comprises at least four openings, wherein each of the at least two distal arms and the at least two proximal arms defines at least one of the at least four opening.

7. The bone fixation device of claim 1, wherein the at least one opening comprises at least two openings, wherein the at least one spine defines the at least two openings.

8. The bone fixation device of claim 1, further comprising at least one arm deformation opening defined in at least one of the at least two distal arms and the at least two proximal arms, wherein the at least one arm deformation opening is configured to facilitate deformation of the at least one of the at least two distal arms and the at least two proximal arms.

9. The bone fixation device of claim 1, wherein the at least one spine comprises a joint or fracture site indicator line.

10. The bone fixation device of claim 1, further comprising at least one arm deformation notch defined in at least one of the at least two distal arms and the at least two proximal arms, wherein the at least one arm deformation notch is configured to facilitate deformation of the at least one of the at least two distal arms and the at least two proximal arms.

11. A bone fixation device comprising:
    (a) a first spine comprising a first curved inner edge and a first outer edge comprising a plurality of notches;
    (b) a second spine comprising a second curved inner edge and a second outer edge comprising a plurality of notches;
    (c) at least two distal arms extending from a distal end of the first and second spines, each of the at least two distal arms comprising at least one distal bone tine, wherein the at least two distal arms are configured to be positionable around a bone;
    (d) at least two proximal arms extending from a proximal end of the first and second spines, each of the at least two proximal arms comprising at least one proximal bone tine, wherein the at least two proximal arms are configured to be positionable around a bone;
    (e) at least one tool interface opening defined in the bone fixation device, wherein the at least one tool interface opening is sized and shaped to receive a portion of an implantation tool; and
    (f) at least one arm deformation feature defined in the bone fixation device, wherein the at least one arm deformation feature is configured to facilitate deformation of at least one of the at least two distal arms and the at least two proximal arms.

12. The bone fixation device of claim 11, wherein the at least one tool interface opening comprises internal threads, wherein the internal threads are configured to receive external threads of the implantation tool.

13. The bone fixation device of claim 11, wherein the at least one tool interface opening comprises at least four openings, wherein each of the at least two distal arms and the at least two proximal arms defines at least one of the at least four tool interface openings.

14. The bone fixation device of claim 11, wherein the at least one arm deformation feature comprises an opening or a notch.

15. The bone fixation device of claim 11, wherein the first and second spines comprise a joint or fracture site indicator line.

16. A bone fixation device comprising:
    (a) at least one spine;
    (b) at least two distal arms extending from a distal end of the at least one spine, each of the at least two distal arms comprising at least one distal deformation control opening, wherein the at least two distal arms are configured to be positionable around a bone; and
    (c) at least two proximal arms extending from a proximal end of the at least one spine, each of the at least two proximal arms comprising at least one proximal deformation control opening, wherein the at least two proximal arms are configured to be positionable around a bone,
    wherein the distal and proximal deformation control openings are configured to facilitate deformation of the at least two distal arms and the at least two proximal arms,
    wherein each of the at least two distal arms and the at least two proximal arms comprise at least one bone tine, wherein each at least one bone tines is positioned at a radius of curvature that is more acute than a radii of curvature within the at least two distal arms and the at least two proximal arms.

17. The bone fixation device of claim 16, wherein the distal and proximal deformation control openings are configured to provide for deformation of the at least two distal arms and the at least two proximal arms in a desired direction.

18. The bone fixation device of claim 16, wherein the distal and proximal deformation control openings are configured to provide for local bend radii of the distal and proximal arms that differ from local bend radii of the distal and proximal arms in the absence of the deformation control openings.

19. The bone fixation device of claim 16, wherein each of the at least two distal arms and the at least two proximal arms comprises:
   (a) a first bend radius imparted around the distal and proximal deformation control openings;
   (b) a second bend radius imparted on the arm between the deformation control opening and a bone tine; and
   (c) a third bend radius imparted on the bone tine.

20. The bone fixation device of claim 19, wherein the first, second, and third bend radii are non-circular in cross-section.

21. A bone fixation kit, comprising:
   (a) a bone fixation device comprising:
      (i) at least one spine;
      (ii) first and second distal arms extending from a distal end of the at least one spine, each of the first and second distal arms comprising at least one distal bone tine; and
      (iii) first and second proximal arms extending from a proximal end of the at least one spine, each of the first and second proximal arms comprising at least one proximal bone tine;
   (b) a support block on which the bone fixation device can be disposed such that the at least one spine, the first and second distal arms, and the first and second proximal arms conform to a shape of the support block; and
   (c) an implantation tool that is coupleable with the first and second distal arms and the first and second proximal arms to remove the bone fixation device from the support block.

22. A bone fixation method, comprising:
providing a bone fixation device comprising:
   (a) at least one spine;
   (b) first and second distal arms extending from a distal end of the at least one spine, each of the first and second distal arms comprising at least one distal bone tine; and
   (c) first and second proximal arms extending from a proximal end of the at least one spine, each of the first and second proximal arms comprising at least one proximal bone tine;

positioning the first and second distal arms around a first target bone site;
crimping the first and second distal arms around the first target bone site with an implantation tool such that the at least one distal bone tine is embedded in the first target bone site;
positioning the first and second proximal arms around a second target bone site; and
crimping the first and second proximal arms around the second target bone site with the implantation tool such that the at least one proximal bone tine is embedded in the second target bone site.

23. The bone fixation method of claim 22, the method further comprising deforming the at least one spine to replicate a natural bend at the first and second target bone sites.

24. The bone fixation method of claim 22, wherein first target bone site comprises a first bone and the second target bone site comprises a second bone, wherein the bone fixation device is positioned across a joint between the first and second bones.

25. The bone fixation method of claim 22, wherein the bone fixation device further comprises at least first and second distal tool interface openings defined in the first and second distal arms and at least first and second proximal tool interface openings defined in the first and second proximal arms, wherein the crimping the first and second distal arms further comprises coupling the implantation tool to the first and second distal tool interface openings, and wherein the crimping the first and second proximal arms further comprises coupling the implantation tool to the first and second proximal tool interface openings.

26. The bone fixation method of claim 22, further comprising coupling the implantation tool to at least first and second distal tool interface openings defined in the first and second distal arms prior to positioning the first and second distal arms around the first target bone site and coupling the implantation tool to at least first and second proximal tool interface openings defined in the first and second proximal arms prior to positioning the first and second proximal arms around the second target bone site.

* * * * *